(12) United States Patent
Sinderby et al.

(10) Patent No.: US 10,376,663 B2
(45) Date of Patent: Aug. 13, 2019

(54) METHOD AND SYSTEM FOR QUANTIFYING TIMING DISCREPANCIES BETWEEN INSPIRATORY EFFORT AND VENTILATORY ASSIST

(71) Applicant: St. Michael's Hospital, Toronto (CA)

(72) Inventors: Christer Sinderby, Toronto (CA); Norman Comtois, Scarborough (CA); Jennifer Beck, Toronto (CA); Pär Emtell, Vällingby (SE); Michael Kock, Akersberga (SE)

(73) Assignee: St. Michael's Hospital, Toronto (CA)

( * ) Notice: Subject to any disclaimer, the term of this patent is extended or adjusted under 35 U.S.C. 154(b) by 718 days.

(21) Appl. No.: 14/355,777

(22) PCT Filed: Nov. 16, 2012

(86) PCT No.: PCT/CA2012/001043
§ 371 (c)(1),
(2) Date: May 1, 2014

(87) PCT Pub. No.: WO2013/071404
PCT Pub. Date: May 23, 2013

(65) Prior Publication Data
US 2014/0296728 A1   Oct. 2, 2014

Related U.S. Application Data

(60) Provisional application No. 61/560,600, filed on Nov. 16, 2011.

(51) Int. Cl.
*A61M 16/00* (2006.01)
*A61B 5/08* (2006.01)
(Continued)

(52) U.S. Cl.
CPC ..... *A61M 16/0051* (2013.01); *A61B 5/04001* (2013.01); *A61B 5/04884* (2013.01);
(Continued)

(58) Field of Classification Search
None
See application file for complete search history.

(56) References Cited

U.S. PATENT DOCUMENTS

| 6,588,423 B1 | 7/2003 | Sinderby |
| 2004/0050387 A1 | 3/2004 | Younes |

(Continued)

FOREIGN PATENT DOCUMENTS

| WO | 2008/131798 | 11/2008 |
| WO | 2010/121313 | 10/2010 |

OTHER PUBLICATIONS

Spahija et al,, "Patient-Ventilator interaction during pressure support ventilation and neurally adjusted ventilaory assist", Critical Care Medicine, vol. 38, No. 2, Feb. 2010, pp. 518-526.

(Continued)

*Primary Examiner* — Etsub D Berhanu
(74) *Attorney, Agent, or Firm* — Fay Kaplun & Marcin, LLP

(57) ABSTRACT

The present disclosure relates to a method and a system for quantifying timing discrepancies between inspiratory effort and ventilatory assist. A trigger error is determined by comparing a start time of neural inspiration with a start time of the ventilatory assist. A cycling-off error is determined by comparing an end time of the neural inspiration with an end time of the ventilatory assist. The ventilatory assist is synchronized when the trigger error is lower than a first threshold and the cycling-off error is lower than a second threshold. The ventilatory assist may also be characterized in terms of early or late trigger and of early or late cycling-off. A trigger of a ventilator may be adjusted according to the trigger error and a cycling-off of a ventilator may be adjusted according to the cycling-off error.

23 Claims, 21 Drawing Sheets

(51) Int. Cl.
*A61B 5/0488* (2006.01)
*A61B 5/04* (2006.01)
*A61B 5/00* (2006.01)

(52) U.S. Cl.
CPC .............. *A61B 5/08* (2013.01); *A61B 5/0809* (2013.01); *A61B 5/742* (2013.01); *A61M 16/00* (2013.01); *A61M 16/0069* (2014.02); *A61M 2016/0021* (2013.01); *A61M 2205/502* (2013.01); *A61M 2210/1014* (2013.01); *A61M 2230/40* (2013.01); *A61M 2230/60* (2013.01)

(56) References Cited

U.S. PATENT DOCUMENTS

2006/0278223 A1   12/2006   Younes
2009/0221926 A1    9/2009   Younes

OTHER PUBLICATIONS

Sassoo, "Triggering of the ventilator in patient-ventilator interactions", Respiratory Care, vol. 56, No. 1, Jan. 2011, pp. 39-51.
Thille et al., "Patient-ventilator asynchrony during assisted mechanical ventilation," Intensive Care Med., No. 32, 2006, pp. 1515-1522.
De Wit et al., "Ineffective triggering predicts increased duration of mechanical ventilation," Crit Care Med., vol. 37, No. 10, 2009, pp. 2740-2745.
De Wit et al., "Observational study of patient-ventilator asynchrony and relationship to sedation level," J Crit Care., No. 24, vol. 1, Mar. 2009, pp. 74-80.
Colombo et al., "Efficacy of ventilator waveforms observation in detecting patient-ventilator asynchrony," Crit Care Med., vol. 39, No. 11, 2011, pp. 2452-2457.
Aldrich et al., "ATS/ERS Statement on respiratory muscle testing," Am J Respir Crit Care Med, vol. 166, 2002, pp. 518-624.
Parthasarathy et al., "Assessment of neural inspiratory time in ventilator-supported patients," Am J Respir Crit Care Med., vol. 162, Aug. 2000, pp. 546-552.
Beck et al., "Characterization of Neural Breathing Pattern in Spontaneously Breathing Preterm Infants," Pediatric Research, vol. 70, No. 6, Dec. 2011, pp. 607-613.

Schmidt et al., "Neurally adjusted ventilatory assist increases respiratory variability and complexity in acute respiratory failure," Anesthesiology, vol. 112, No. 3, Mar. 2010, pp. 670-681.
Colombo et al., "Physiologic response to varying levels of pressure support and neurally adjusted ventilatory assist in patients with acute respiratory failure," Intensive Care Med., vol. 36, No. 11, 2008, pp. 2010-2018.
Pohlman et al., "Excessive tidal volume from breath stacking during lung-protective ventilation for acute lung injury," Crit Care Med., vol. 36, No. 11, 2008, pp. 3019-3023.
Beck et al., "Prolonged neural expiratory time induced by mechanical ventilation in infants," Pediatric Research, vol. 55, No. 5, May 2004, pp. 747-754.
Moerer et al., "Subject-ventilator synchrony during neural versus pneumatically triggered non-invasive helmet ventilation," Intensive Care Med., vol. 34, No. 9, Sep. 2008, pp. 1615-1623.
Bordessoule et al., "Neurally Adjusted Ventilatory Assist (NAVA) improves patient-ventilator interaction in infants compared to conventional ventilation," Pediatric Research, vol. 72, No. 2, Aug. 2012, pp. 194-202.
Sinderby et al., "Proportional assist ventilation and neurally adjusted ventilatory assist—better approaches to patient ventilator synchrony," Clin Chest Med., vol. 29, No. 2, Jun. 2008, pp. 329-342.
Laurence Vignaux et al., "*Patient-ventilator asynchrony during non-invasive ventilation for acute respiratory failure: a multicenter study*", Intensive Care Med (2009) 35:840-846 DOI 10.1007/s00134-009-1416-5, pp. 840-846.
Doorduin et al., "Automated patient-ventilator interaction analysis during neurally adjusted non-invasive ventilation and pressure support ventilation in chronic obstructive pulmonary disease", Critical Care, vol. 18, No. 550, Oct. 2014, 8 sheets.
Dres et al., "Monitoring patient-ventilator asynchrony", Current Opinion, vol. 22, No. 3, Jun. 2016, pp. 246-253.
Koopman et al., "Transcutaneous electromyographic respiratory muscle recordings to quantify patient-ventilator interaction in mechanically ventilated children", Annals of Intensive Care, vol. 8, No. 12, Jan. 2018, 9 sheets.
Mortamet et al., "Patient-ventilator asynchrony during conventional mechanical ventilation in children", Annals of Intensive Care, vol. 7, No. 122, Dec. 2017, 11 sheets.
Sinderby et al., "An automated and standardized neural index to quantify patient-ventilator interaction", Critical Care, vol. 17, No. R239, Oct. 2013, 9 sheets.

METHOD AND SYSTEM FOR QUANTIFYING TIMING DISCREPANCIES BETWEEN INSPIRATORY EFFORT AND VENTILATORY ASSIST

TECHNICAL FIELD

The present disclosure relates to the field of ventilatory assist. More specifically, the present disclosure relates to a method and a system for quantifying timing discrepancies between inspiratory effort and ventilatory assist.

BACKGROUND

Detection and quantification of asynchronies between inspiratory effort and ventilatory assist during mechanical ventilation is complicated. A first relevant information element concerns patient's neural inspiratory effort. Most methods of determining inspiratory effort use the onset of inspiratory pressure, flow, and/or volume or any related integral or derivative thereof to assess the start and end of inspiration. Due to many factors related to respiratory muscle weakness and impaired respiratory mechanics, there are limitations as to the level of disability where pneumatic measurements are of value. Intrathoracic measurement of inspiratory pressures is another approach to determine the start and end of an inspiratory effort. This approach is limited by (a) the use of expiratory muscles, falsely indicating a negative pressure deflection although neural inspiration has not yet commenced as well as (b) application of ventilatory assist that causes the nadir of the negative pressure deflection to occur more and more prematurely as ventilatory assist increases.

Measuring the electrical activity of inspiratory (or related to inspiration) muscles offers an approach that is more directly related to neural activity of respiratory muscles. There are, however, limitations as to how one can reliably obtain these electrical signals. Electrodes placed on the surface of the thorax or neck region may record inspiratory muscle electrical activity, but may also record activity related to posture and active expiration. Signals obtained in the esophagus, at the level of the diaphragm hiatus, reflect diaphragm electrical activity (EAdi), but may include crosstalk from the esophagus itself, its lower sphincter, and the heart.

A second information element relevant to determining patient ventilator asynchrony is the start and termination of the ventilatory assist. Obtaining this information is relatively easy since (a) the state of the mechanical ventilator can be acquired directly from the machine, or (b) the onset of pressure deflection can be detected by measuring pressure/flow/volume signals from the ventilator circuit.

In general, the patient-ventilator asynchrony is related to delays between the onset of neural inspiratory effort and the onset of ventilatory assist as well as between the end of the neural inspiratory effort and the termination of the ventilatory assist. Thus, the asynchrony can relate to (1) ventilatory assist starting before neural inspiratory effort (early triggering) and (2) ventilatory assist starting after neural inspiratory effort (late triggering). Also, the asynchrony can relate to (3) ventilatory assist terminating before neural inspiratory effort (early off-cycling) and (4) ventilatory assist terminating after neural inspiratory effort (late off-cycling). In the extreme, there could be (5) a neural inspiratory effort without any delivery of mechanical ventilatory assist (wasted inspiratory effort) or (6) a full cycle of ventilatory assist delivered in the absence of neural inspiratory effort (auto-triggering). There could also be several cycles of ventilatory assist during a single cycle of neural inspiratory effort or vice versa. Currently there is no efficient method for determining and quantifying all of these situations.

Therefore, there is a need for a standardized and non-biased technique for automatically determining and quantifying asynchronies between inspiratory effort and ventilatory assist during mechanical ventilation. Reliable information can then be used to correct errors in the ventilator settings or indicate need for change of ventilator mode.

SUMMARY

According to the present disclosure, there is provided a method of quantifying timing discrepancies between a patient's inspiratory effort and ventilatory assist to the patient. An early or late trigger error is determined by comparing a start time of neural inspiration with a start time of the ventilatory assist. An early or late cycling-off error is determined by comparing an end time of the neural inspiration with an end time of the ventilatory assist. Determination is then made that the ventilatory assist is synchronized when the trigger error is lower than a first threshold and the cycling-off error is lower than a second threshold.

According to the present disclosure, there is also provided a system for quantifying timing discrepancies between a patient's inspiratory effort and ventilatory assist to the patient by a ventilator. The system comprises means for measuring a neural inspiration of the patient. The system also comprises a processor. The processor operates the following functions: determining an early or late trigger error by comparing a start time of the neural inspiration with a start time of the ventilatory assist, determining an early or late cycling-off error by comparing an end time of the neural inspiration with an end time of the ventilatory assist, and determining that the ventilatory assist is synchronized when the trigger error is lower than a first threshold and the cycling-off error is lower than a second threshold.

The present disclosure further relates to a system for quantifying timing discrepancies between a patient's inspiratory effort and ventilatory assist to the patient. A first interface is configured to receive, from one or more electrodes, a neural inspiration signal representing patient's inspiratory effort. A second interface is configured to receive, from a mechanical ventilator, a measurement signal representing a start time and an end time of the ventilatory assist. A processor is operatively coupled to the first and second interfaces. The processor is configured to determine an early or late trigger error by comparing a start time of the neural inspiration with the start time of the ventilatory assist, determine an early or late cycling-off error by comparing an end time of the neural inspiration with the end time of the ventilatory assist, and determine that the ventilatory assist is synchronized when the trigger error is lower than a first threshold and the cycling-off error is lower than a second threshold.

The present disclosure also provides a method of quantifying timing discrepancies between a patient's inspiratory effort and ventilatory assist to the patient. An absolute trigger error is determined as a start time of the ventilatory assist minus a start time of neural inspiration within an inspiratory test period. If the absolute trigger error is a negative value, a relative asynchrony for an early trigger is determined by normalizing the absolute trigger error to a duration between a start time of the inspiratory test period and the start time of the ventilatory assist. If the absolute trigger error is a positive value, a relative asynchrony for a late trigger is determined by normalizing the absolute trigger error to a duration between the start time of the ventilatory assist and an end time of the inspiratory test period.

The present disclosure further provides a method of quantifying timing discrepancies between a patient's inspiratory effort and ventilatory assist to the patient. An absolute cycling-off error is determined as an end time of the ventilatory assist minus an end time of neural inspiration within an expiratory test period. If the absolute cycling-off error is a negative value, a relative asynchrony for an early cycling-off is determined by normalizing the absolute cycling-off error to a duration between a start time of the expiratory test period and an end time of the ventilatory assist. If the absolute cycling-off error is a positive value, a relative asynchrony for a late cycling-off is determined by normalizing the absolute cycling-off error to a duration between the end time of the ventilatory assist and an end time of the expiratory test period.

The foregoing and other features will become more apparent upon reading of the following non-restrictive description of illustrative embodiments thereof, given by way of example only with reference to the accompanying drawings.

BRIEF DESCRIPTION OF THE DRAWINGS

Embodiments will be described in the present disclosure by way of example only with reference to the accompanying drawings, in which.

DETAILED DESCRIPTION

Figure 1:
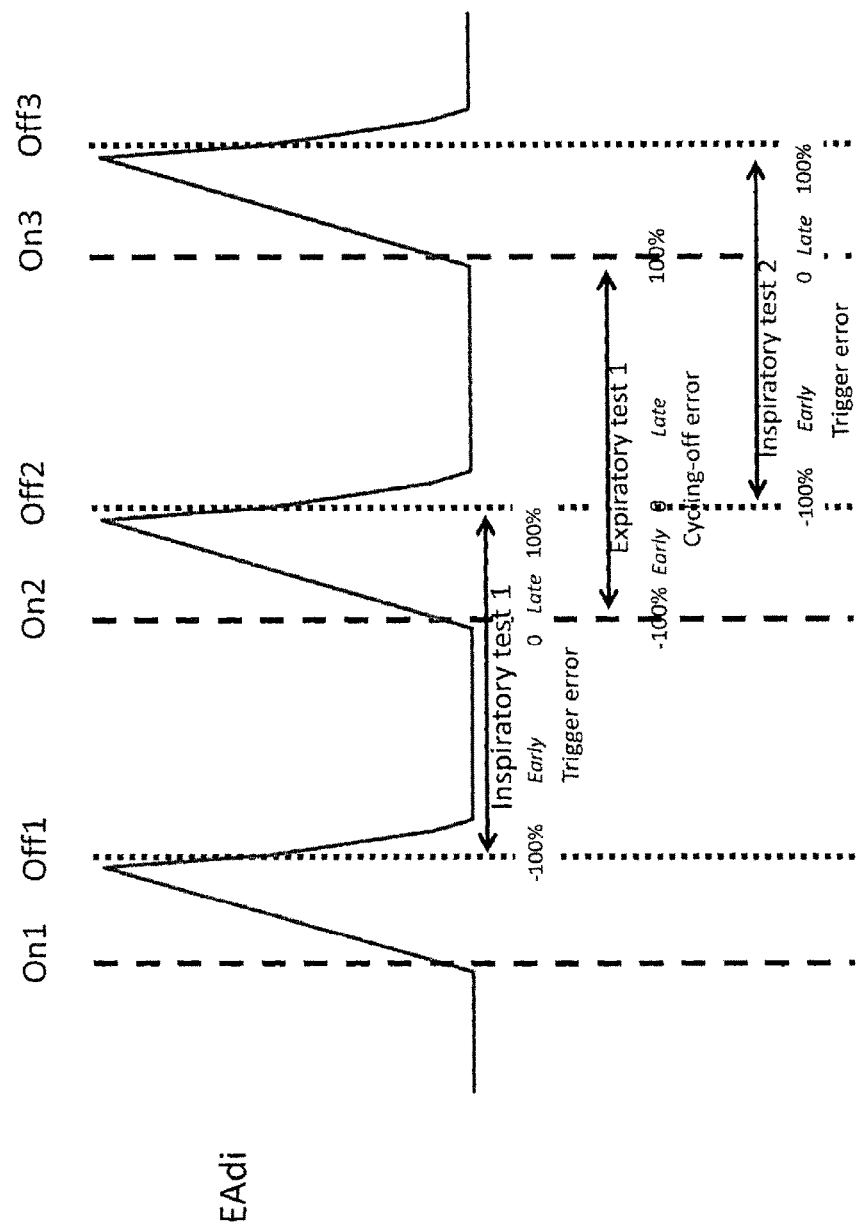
FIG. 1 is a schematic tracing of diaphragm electrical activity (EAdi)

Various aspects of the present disclosure generally address one or more of the problems of determining and quantifying asynchronies between patient's inspiratory effort and ventilatory assist during mechanical ventilation.

The following terminology is used throughout the present disclosure:

Ventilatory assist: provision of a flow or air, a flow of oxygen or other medical gases, an air pressure, or an oxygen or other medical gas pressure to a patient for helping a respiratory function of the patient.

Ventilator: apparatus or system for providing ventilatory assist to a patient.

Timing discrepancy: lack of alignment between two related events, asynchrony.

Neural inspiratory effort: a patient's exertion of respiratory muscles, including generation of an inspiratory pressure or any other action from respiratory muscles.

Neural inspiration: nervous system control of respiratory muscles.

Trigger error: timing discrepancy between a start time of neural inspiration and a start time of ventilatory assist.

Cycling-off error: timing discrepancy between an end time of neural inspiration and an end time of ventilatory assist.

Diaphragm electrical activity (EAdi): measurable electrical activity of a patient's diaphragm.

Electrode: a conductor capable of acquiring a signal from a patient's body part.

Computer: an electronic device or a combination of electronic devices capable of processing information.

Interface: a communication endpoint of a computer capable of receiving and sending signals over any one of a variety of communication media.

Processor: an electronic circuit or a combination of electronic circuits capable of processing information, including but not limited to a central processing unit, a microprocessor, a graphics processing unit, a digital signal processor, and the like.

DESCRIPTION OF EMBODIMENTS

The present disclosure introduces a method and a system for quantifying timing discrepancies between a patient's inspiratory effort and ventilatory assist to the patient. The method and system may provide a direct overview in one single graphical representation, for example using a comprehensive asynchrony index, called "NeuroSync Index" for patient-ventilator interaction. The method and system may be used to adjust ventilatory assist and/or trigger and cycling-off sensitivity to improve ventilatory assist.

A reliable source of information of patient's neural inspiratory effort may be obtained, for example using a diaphragm electrical activity (EAdi) reading as taught in U.S. Pat. No. 6,588,423 to Sinderby, the disclosure of which is incorporated herein by reference. Sinderby teaches examples of neural trigger and cycling-off criteria using the EAdi signal. Detection of a start time of neural inspiration may be made by detecting any significant positive deflection in EAdi that fulfils a set of criteria related to a neural inspiratory effort, for example a μV increase in EAdi. Detection of an end time of neural inspiration may be made by determining when the neural inspiratory signal, for example the EAdi, has decreased to a defined percentage of peak EAdi activity. Of course any other method reliably determining the start time and end time of neural inspiration may be used.

A second variable useful to determine patient's ventilator asynchrony is the start time and end time of the ventilatory assist. As expressed hereinbefore, this information may be obtained from the state of the mechanical ventilator, which may be acquired directly from the machine. Alternatively, the onset of pressure deflection may be detected by measuring pressure/flow/volume signals from the ventilatory circuit. Of course any other method reliably determining the start time and end time of the ventilatory assist may be used.

Referring now to the drawings, FIG. 1 is a schematic tracing of diaphragm electrical activity (EAdi). Neural inspiratory effort is expressed as increased EAdi readings between On1 and Off1, On2 and Off2, as well as On3 and Off3. Two inspiratory test periods, used to determine early or late triggering, are illustrated between Off1 and Off2 as well as between Off2 and Off3. An expiratory test period, used to determine early or late cycling-off, is illustrated between On2 and On3. As depicted in FIG. 1, the periods expressing early and late trigger and cycling-off errors may be expressed in percentages, where negative values express early trigger and cycling-off errors and positive values express late trigger and cycling-off errors.

FIGS. 2-7 presented hereinbelow each comprise an upper half showing a schematic tracing of ventilatory assist, for example positive-pressure ventilatory assist, delivered to a patient by a mechanical ventilator (Pvent) while a lower half shows an EAdi tracing, which may be compared to that of FIG. 1.

Figure 2:
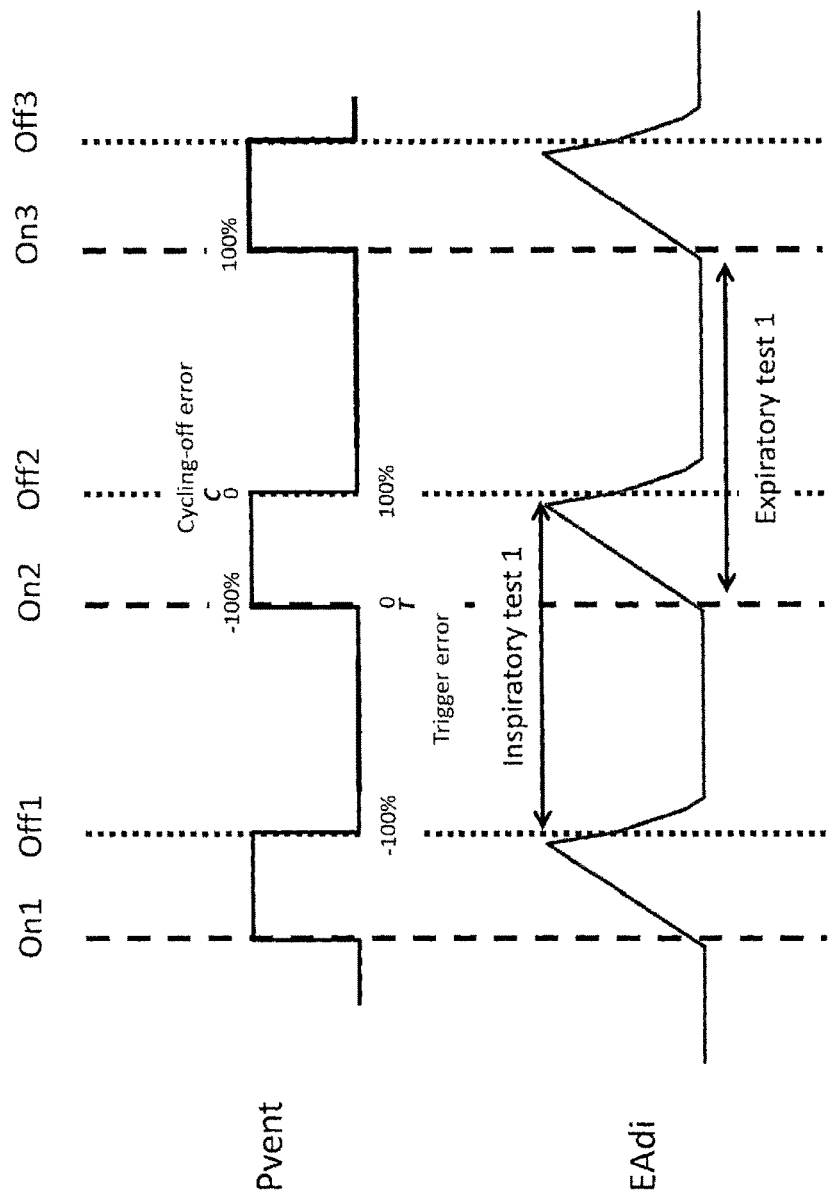
FIG. 2 is a diagram showing an example of synchronized ventilatory assist.

FIG. 2 is a diagram showing an example of synchronized ventilatory assist. An increased EAdi is visible between On1 and Off1, On2 and Off2, as well as On3 and Off3, indicating that EAdi increases when ventilatory assist is delivered. Inspiratory test 1 is shown between Off1 and Off2. The symbol T shows that the ventilatory assist (Pvent) starts at time On2, which is the onset of the patient's neural inspiratory effort or the start time of neural inspiration and represents 0% trigger error for inspiratory test 1. The expiratory test 1 is indicated between On2 and On3. The symbol C shows that the ventilatory assist (Pvent) ends at time Off2, which is at the end of the patient's neural inspiratory effort or the end time of neural inspiration and represents 0% cycling-off error for expiratory test 1. The end of the patient's neural inspiratory effort may be detected when reaching, for example, about 70% of the EAdi peak.

Figure 3:
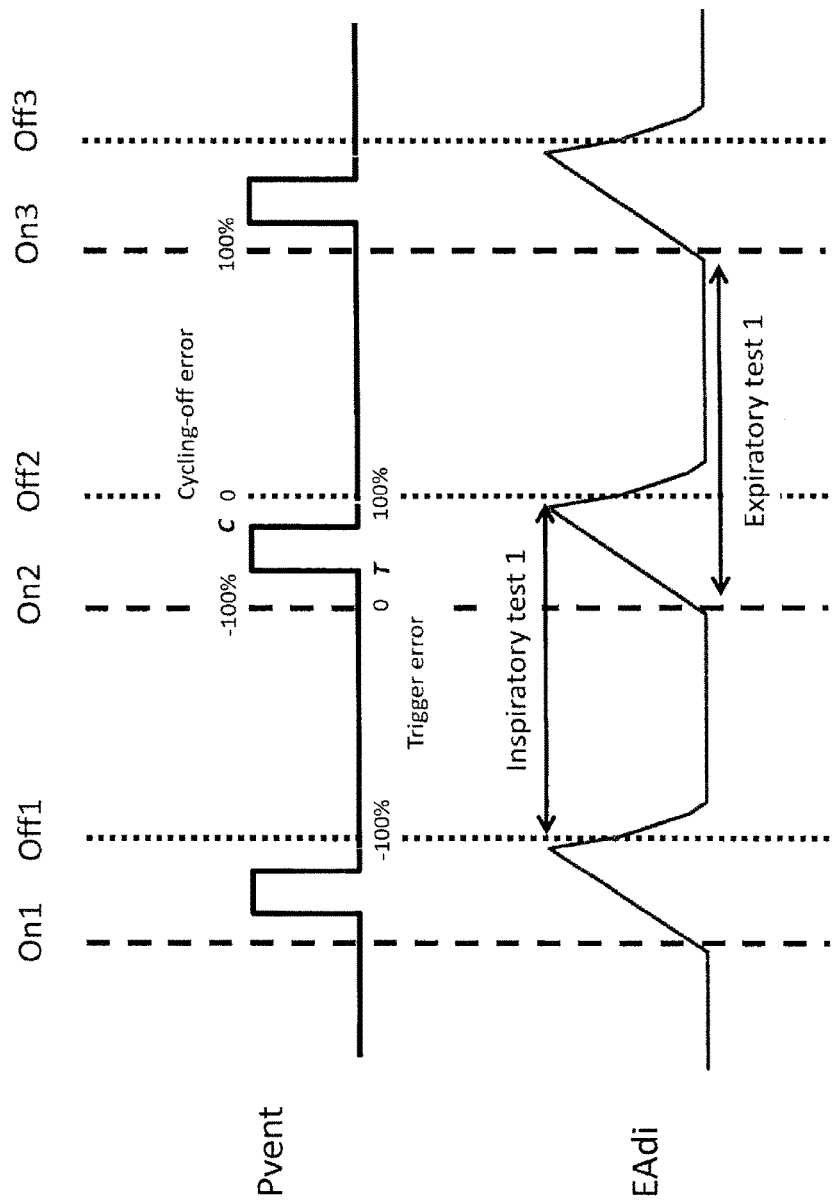
FIG. 3 is a diagram showing an example of non-synchronized ventilatory assist showing late trigger and early cycling-off.

FIG. 3 is an example of non-synchronized ventilatory assist showing late trigger and early cycling-off. The symbol T shows that the ventilatory assist (Pvent) starts at a time later than On2, and represents a late (positive % value) trigger error for inspiratory test 1. The symbol C shows that the ventilatory assist (Pvent) ends at a time earlier than Off2, and represents an early (negative % value) cycling-off error for expiratory test 1.

Figure 4:
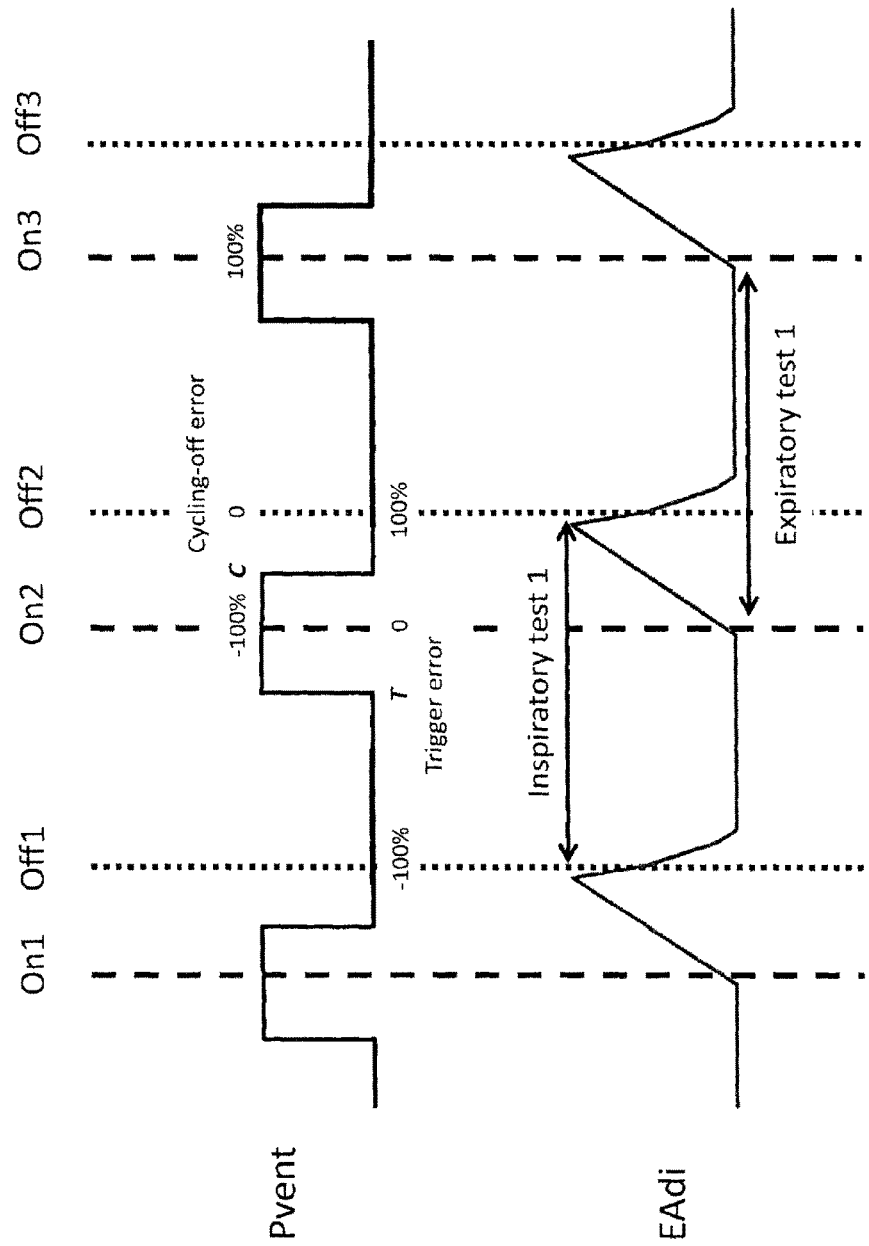
FIG. 4 is a diagram showing an example of non-synchronized ventilatory assist showing early trigger and early cycling-off.

FIG. 4 is an example of non-synchronized ventilatory assist showing early trigger and early cycling-off. The symbol T shows that the ventilatory assist (Pvent) starts at a time earlier than On2, and represents an early (negative % value) trigger error for inspiratory test 1. The symbol C shows that the ventilatory assist (Pvent) ends at a time earlier than Off2, and represents an early (negative % value) cycling-off error for expiratory test 1.

Figure 5:
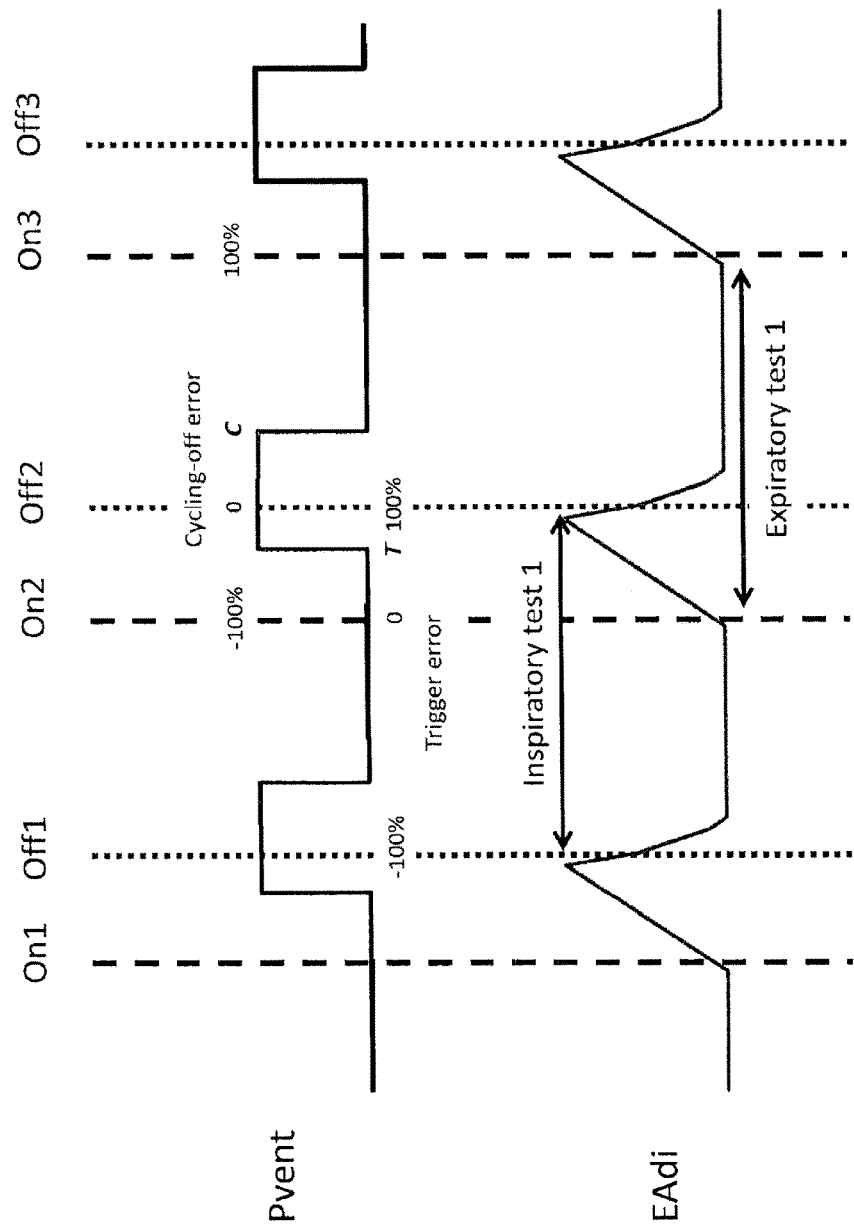
FIG. 5 is a diagram showing an example of non-synchronized ventilatory assist showing late trigger and late cycling-off.

FIG. 5 is an example of non-synchronized ventilatory assist showing late trigger and late cycling-off. The symbol T shows that the ventilatory assist (Pvent) starts at a time later than On2, and represents a late (positive % value) trigger error for inspiratory test 1. The symbol C shows that the ventilatory assist (Pvent) ends at a time later than Off2, and represents a late (positive % value) cycling-off error for expiratory test 1.

Figure 6:
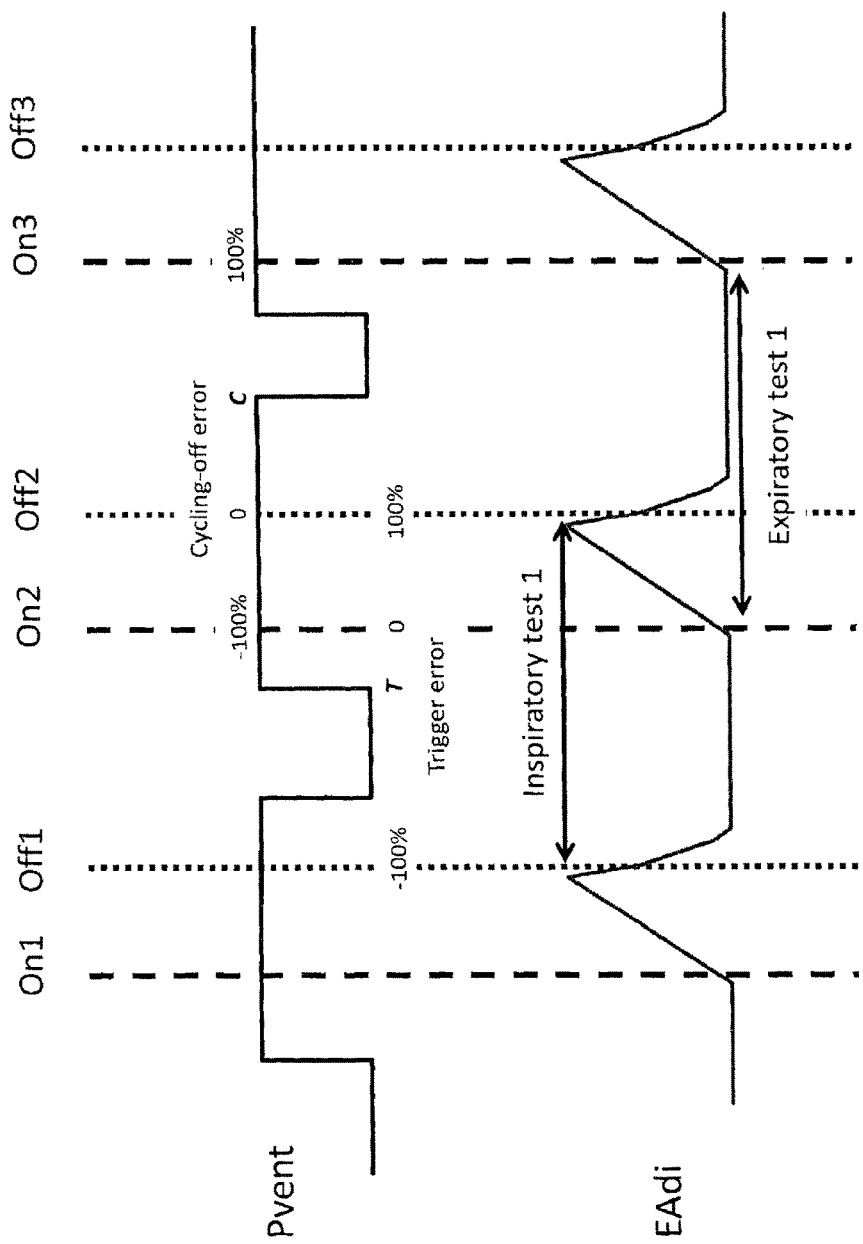
FIG. 6 is a diagram showing an example of non-synchronized ventilatory assist showing early trigger and late cycling-off.

FIG. 6 is an example of non-synchronized ventilatory assist showing early trigger and late cycling-off. The symbol T shows that the ventilatory assist (Pvent) starts at a time earlier than On2, and represents an early (negative % value) trigger error for inspiratory test 1. The symbol C shows that the ventilatory assist (Pvent) terminates at a time later than Off2, and represents a late (positive % value) cycling-off error for expiratory test 1.

Figure 7:
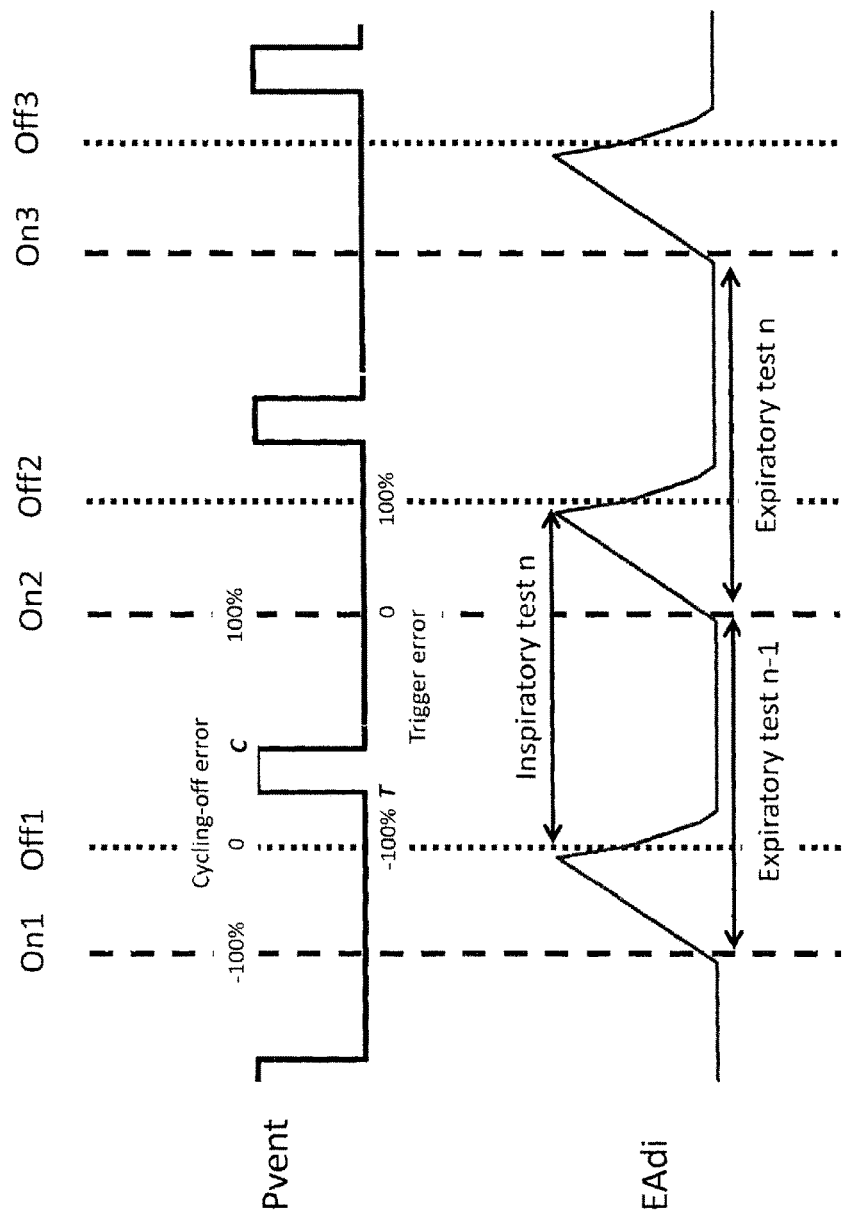
FIG. 7 is a diagram showing an example of non-synchronized ventilatory assist showing a second case of late trigger and late cycling-off.

FIG. 7 is a diagram showing an example of non-synchronized ventilatory assist showing a second case of late trigger and late cycling-off. The symbol T shows that the ventilatory assist (Pvent) starts at a time earlier than On2, and represents an early (negative % value) trigger error for inspiratory test n. In this case, the expiratory test of the preceding breath (Expiratory test n−1) is indicated between On1 and On2. The symbol C shows that the ventilatory assist (Pvent) ends at a time later than Off1, which is at the end of the neural inspiratory effort—of the preceding breath—and represents a late (positive % value) cycling-off error for expiratory test n−1.

In view of the above Figures, determination of error to trigger the ventilatory assist may be based on examination of a neural inspiratory test period starting from the termination of the previous neural inspiratory effort (Off1 in FIGS. 1-7) and ending at the termination of the following neural inspiratory effort (Off2 in FIGS. 1-7). As expressed hereinabove, definition of neural inspiration termination may be based on a percentage of peak neural activity, for example on a percentage of peak EAdi. If desired, the peaks and nadirs of the neural inspiratory effort may be retraced from the points described above. During each neural inspiratory test period, the actual start time of ventilatory assist may be detected between two points e.g. Off1 and Off2 for inspiratory test 1 in FIGS. 2-7.

Disturbances from cardiac (ECG) signals on the EAdi may, if occurring at the start time or the end time of ventilatory assist, cause uncertainty of accuracy in error determination. Thus, situations where ECG signals coincide with trigger should be avoided by detecting the ECG period and compare its timing to the ventilatory assist start time and end time. If timing of ECG coincides with the ventilatory assist start time or end time, synchrony analysis should be avoided. Of course in a situation where no disturbances from ECG occur this would not be necessary.

An adequate triggering may be defined as the start time of the ventilatory assist occurring substantially at the same time as the neural inspiration starts, indicated in FIG. 2 by T at On2 for inspiratory test 1, providing close to 0 trigger error. Early triggering may be defined as the start time of the ventilatory assist occurring at a time before the neural inspiration starts, indicated in FIGS. 4, 6 and 7 by T occurring before On2 for inspiratory test 1, resulting in a negative percentage trigger error. Late triggering may be defined as the start time of the ventilatory assist occurring at a time later than the neural inspiration starts, indicated in FIGS. 3 and 5 by T occurring later than On2 for inspiratory test 1, resulting in a positive percentage trigger error. An adequate cycling-off may be defined as the end time of the ventilatory assist occurring substantially at the same time as the neural inspiration ends, indicated in FIG. 2 by C at Off2 for expiratory test 1, providing close to 0% cycling-off error. Early cycling-off may be defined as the end time of the ventilatory assist occurring at a time before the neural inspiration ends, indicated in FIGS. 3 and 4 by C occurring before Off2 for expiratory test 1, resulting in a negative percentage cycling-off error. Late cycling-off may be defined as the end time of the ventilatory assist occurring at a time later than the neural inspiration ends, indicated in FIGS. 5 and 6 by C occurring at a time later than Off2 for inspiratory test 1 or in FIG. 7 by C occurring later than Off1 for inspiratory test n−1, resulting in a positive percentage cycling-off error. Wasted inspiratory effort, defined as neural inspiratory effort without assistance from the ventilator, will be given trigger and cycling-off errors values of 100%, respectively.

Using the examples of FIGS. 2-7, a trigger error may be determined in absolute units by calculating:

$$\text{Absolute trigger error} = T - On2$$

wherein:

T is the time of starting the ventilatory assist; and
On2 is the start time of neural inspiration.

If the absolute trigger error is a negative value the relative asynchrony for the early trigger may be determined by normalizing the absolute trigger error to the duration between Off1 and On2. If the absolute trigger error is a positive value the relative asynchrony for the late trigger may be determined by normalizing the absolute trigger error to the duration between On2 and Off2. In this way early trigger error may be recognized by a negative value whereas late trigger error will have a positive value. Alternatively, the relative trigger error may be replaced by the absolute numbers as well as by logarithmic, exponential or power functions of these numbers.

Using the examples of FIGS. 2-7, a cycling-off error may be determined in absolute units by calculating:

$$\text{Absolute cycling-off error} = C - Off2$$

wherein:

C is the time for termination or ending of the ventilatory assist; and
Off2 is the time of ending of neural inspiration.

If the absolute cycling-off error is a negative value the relative asynchrony for the early cycling-off may be determined by normalizing the absolute cycling-off error to the duration between On2 and Off2. If the absolute cycling-off error is a positive value the relative asynchrony for the late cycling-off may be determined by normalizing the absolute cycling-off error to the duration between Off2 and On3. In this way early cycling-off will be recognized by a negative value whereas late cycling-off error will have a positive value. Alternatively, the relative cycling-off error may be replaced by the absolute numbers as well as by logarithmic, exponential or power functions of these numbers.

Figure 8:
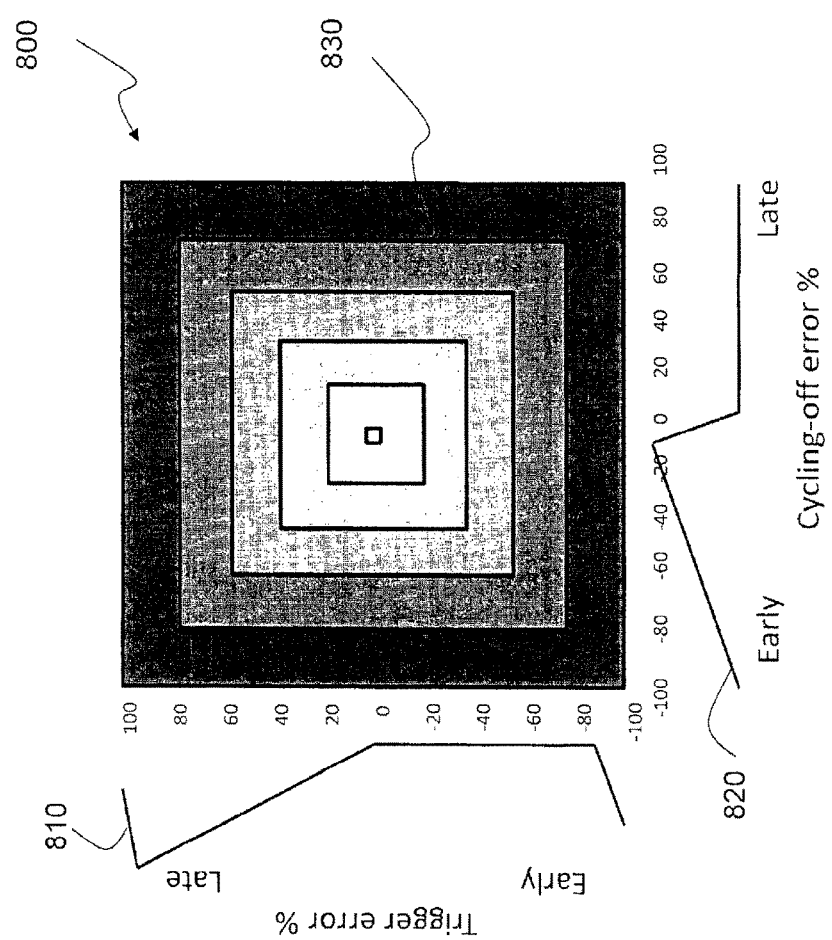
FIG. 8 is a graph illustrating a method for graphically displaying related values for trigger and cycling-off errors.

Values for inspiratory and expiratory tests corresponding to Inspiratory test 1 and Expiratory test 1 in FIGS. 2-6 as well as to Inspiratory test n and Expiratory test n−1 in FIG. 7 may be presented graphically. FIG. 8 is a graph illustrating a method for graphically displaying related values for trigger and cycling-off errors. Graphical display of trigger and cycling-off errors as shown on FIG. 8 and on some of the following Figures allow characterizing the ventilatory assist. On graph 800, trigger errors are represented, in percentage, on the ordinate and cycling-off errors are represented, in percentage, on the abscissa. Inspiration values 810 and expiration values 820 are also represented, along the ordinate and the abscissa respectively. Square concentric boxes 830 represent combined trigger and cycling-off errors, with increasing errors landing towards external margins of the graph 800, whereas synchronized ventilatory assist lands near the center of the graph 800. Boxes 830 are based on percent error in triggering and cycling-off and indicate the degree of the asynchrony. Each corner of the graph 800 represents the worst case scenario of error in triggering and cycling-off whereas the center of the graph 800 indicates perfect synchrony.

Figure 9:
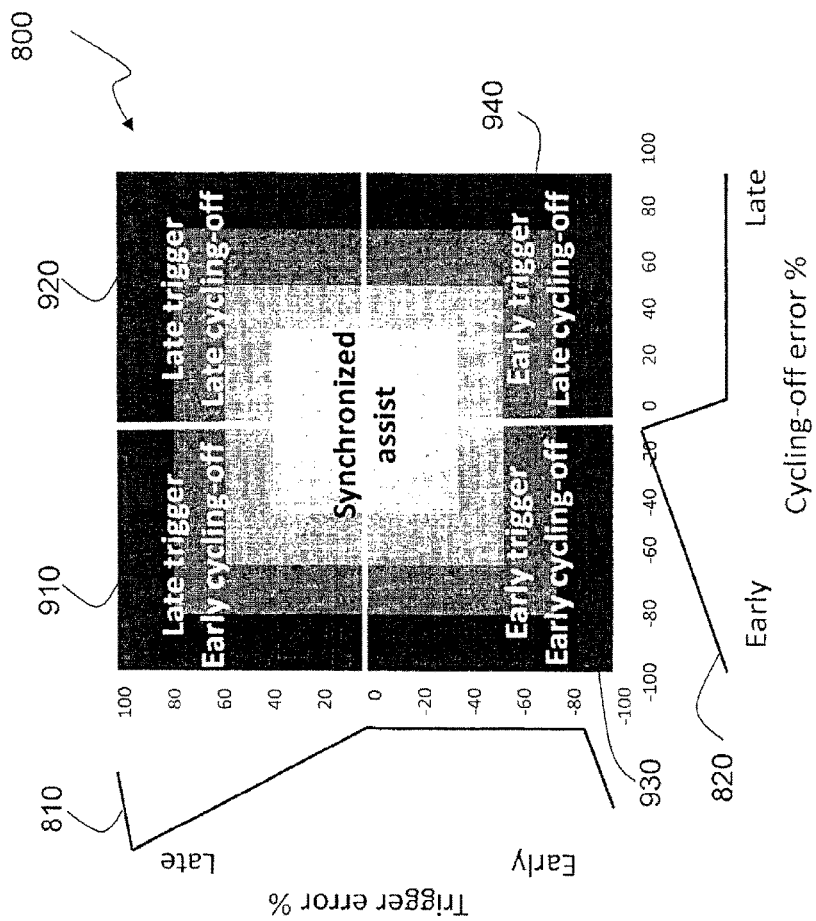
FIG. 9 is a graph illustrating an application of the method of FIG. 8.

FIG. 9 illustrates an application of the method of FIG. 8. Quadrants where the trigger errors exemplified in FIGS. 2-7 occur are indicated. Synchronized trigger and cycling-off will be plotted near the center of the graph 800. Upper left quadrant 910 indicates late trigger and early cycling-off, a condition that may be seen, for example, in prematurely born babies. Upper right quadrant 920 indicates late trigger and late cycling-off, a condition that may be seen, for example, in adult patients with obstructive lung disease. Lower left quadrant 930 indicates early trigger and early cycling-off, a rather extreme condition that may be associated, for example, with too sensitive trigger settings in very small babies or very stiff lungs. Lower right quadrant 940 indicates early trigger and late cycling-off, a condition often resulting, for example, from too sensitive trigger setting or leaks in the respiratory circuit. The center of the graph 800 represents perfect synchrony between ventilatory assist and neural inspiratory effort.

Figure 10:
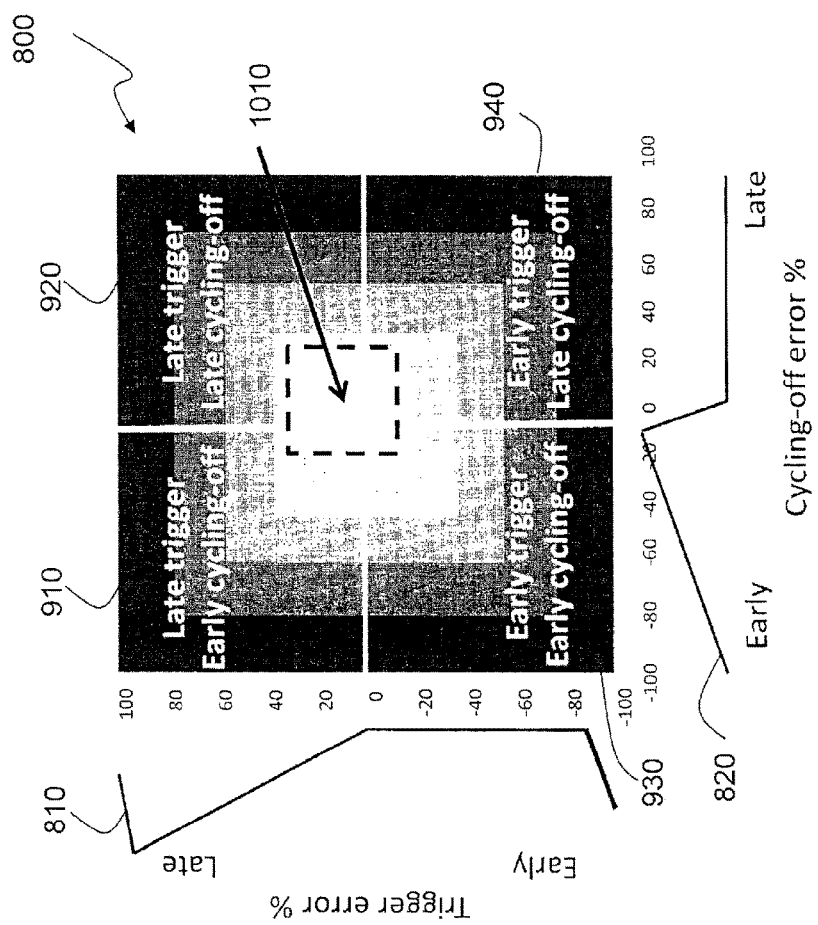
FIG. 10 is a graph showing a zone of acceptable synchrony in the method of FIG. 8.

FIG. 10 shows a zone of acceptable synchrony in the method of FIG. 8. An area 1010 indicating acceptable trigger and cycling-off errors, also referred to as acceptable synchrony, is illustrated. In an embodiment, acceptable synchrony may be observed when the trigger error is smaller than an error threshold while the cycling-off error is smaller than the same or another error threshold. In the example of the area 1010, four (4) different error thresholds may be used, wherein an error threshold for an acceptable early trigger is smaller than an error threshold for an acceptable late trigger and wherein an error threshold for an acceptable early cycling-off is smaller than an error threshold for an acceptable late cycling-off. The position of the area 1010 on the graph 800 is however presented as a non-limiting example and other error threshold combinations may be used depending on the needs of a patient.

A ratio of patient's inspirations falling within the area 1010 of acceptable synchrony relative to patient's inspirations falling outside the area 1010 of acceptable synchrony may be calculated to quantify an acceptable and an unacceptable level of trigger and cycling-off errors in a single value. A zone of acceptable synchrony (tolerable trigger and cycling-off errors) can be applied. Calculating the ratio between acceptable synchrony, defined as tolerable levels of trigger and cycling-off errors, and unacceptable asynchrony, defined as intolerable levels of trigger and cycling-off errors, provides the above mentioned NeuroSync Index, which is a unique index to quantify the success with which the ventilatory assist is delivered.

Figure 11:
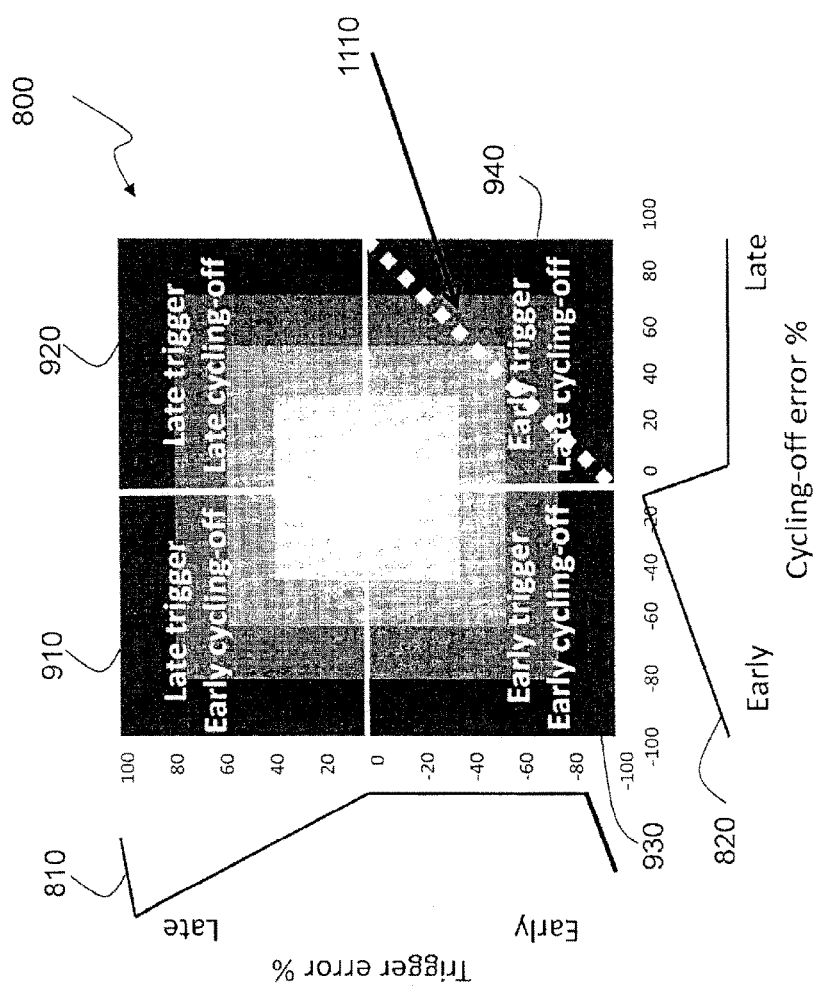
FIG. 11 is a graph showing an area of ventilatory assist during central apnea as determined by the method of FIG. 8.

FIG. 11 shows an area of ventilatory assist during central apnea as determined by the method of FIG. 8. A diagonal dotted line in the lower right quadrant 940 indicates an area 1110 where ventilatory assist during central apnea will appear. More specifically, breaths related to ventilatory assist during central apnea occur as a diagonal band in the lower right quadrant 940.

The information from the above described method may be used to set tolerance levels for adequate ventilatory assist and to instruct to perform manual or automatic, adjustments to improve synchrony.

By determining threshold levels for early and late trigger and cycling-off errors (see box or area 1010 of FIG. 10 indicating acceptable synchrony) and calculating a ratio between occurrences or breaths that fall within and outside the area 1010, it is possible to determine a ratio between acceptable synchrony and non-acceptable asynchrony. A value close to 1 would indicate near all breath are assisted with acceptable synchrony, whereas a value close to 0 suggest that near all breaths have poorly synchronized ventilatory assist, i.e. non-acceptable asynchrony. A cut-off value can be set between these extremes and if the value of the NeuroSync Index is lower than the cut-off value an alarm can be triggered and a sequence to correct the error can be initiated.

To determine the nature of the problem, early trigger errors, late trigger errors, early cycling-off errors, and late cycling-off errors falling outside acceptable error limits (indicated by the box or area 1010 in FIG. 10) may be counted. Naturally the counts can be normalized to total counts including or excluding the acceptable synchrony (indicated by the box or area 1010 in FIG. 10). The highest count indicates the most frequent error, the lowest the least frequent error. Comparison of these counts would make it possible to obtain the prevalence of each error and the order of which error is most frequent, second most frequent and so on.

A procedure could then be initiated with instructions for manual or automatic adjustments to correct these errors. For example instructions or actions could be as follows:

Early trigger error—decrease trigger sensitivity
Late trigger error—increase trigger sensitivity
Early cycling-off error—decrease cycling-off sensitivity
Late cycling-off error—increase cycling-off sensitivity After a period, if the manual or automatic adjustments result in an acceptable ratio between acceptable synchrony and non-acceptable asynchrony no further actions are required.

If the problem persists and indicates the same type of error, the instructions or actions (manual or automatic adjustments) to correct these errors could be repeated.

Also, other instructions or actions such as:

Early trigger error—test for leak
Late trigger error—reduce assist level
Late cycling-off error—reduce assist level could be introduced in a stepwise fashion.

Figure 12:
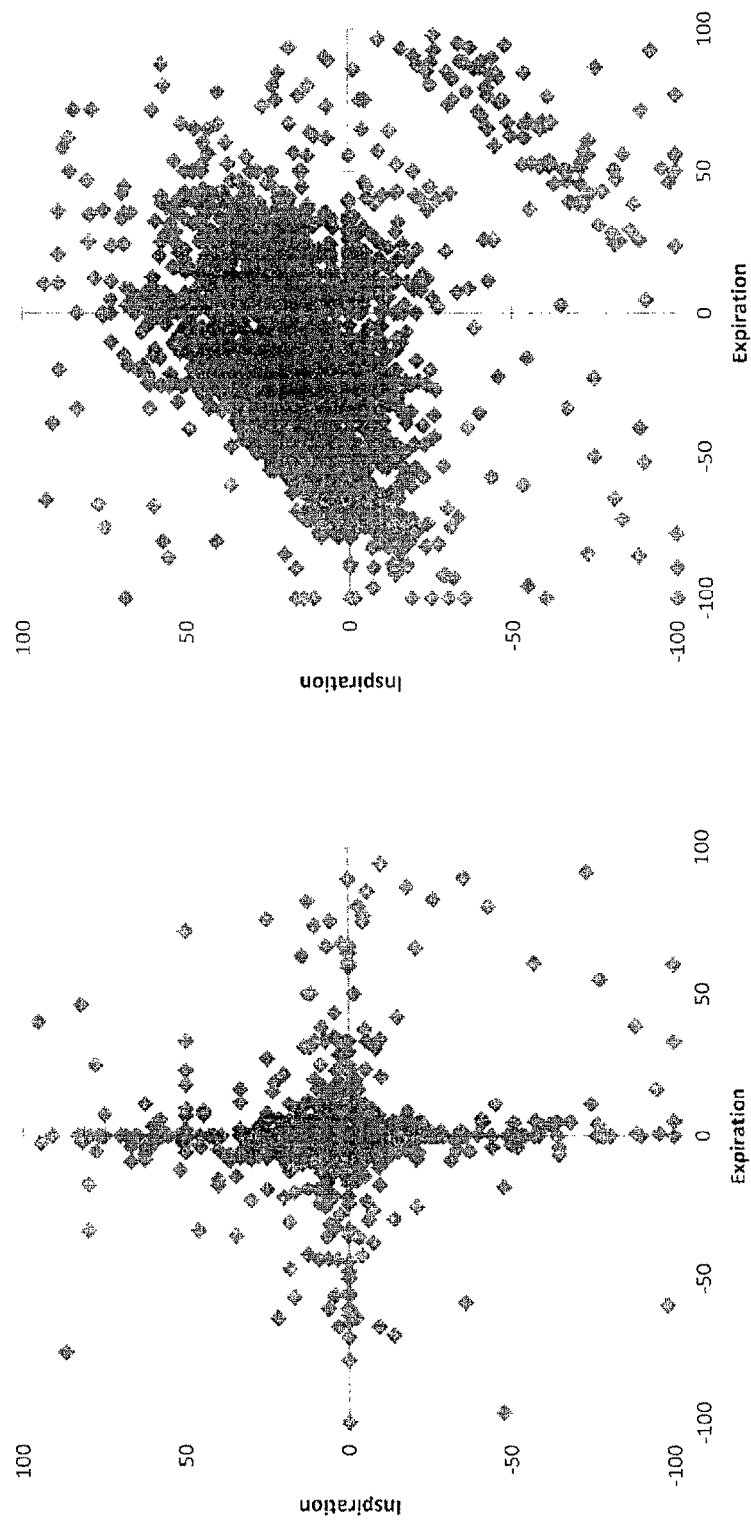
FIG. 12 represents graphs showing real examples of values for trigger and cycling-off errors obtained in a premature baby.

FIG. 12 shows real examples of values for trigger and cycling-off errors obtained in a premature baby. Each data point shown on the Figure indicates one breath of a real example. On the left-hand side of FIG. 12, good synchrony with Neurally Adjusted Ventilatory assist is observable since a majority of trigger and cycling-off errors are located close to center of graph. The right-hand side of FIG. 12 shows poor synchrony during "Synchronized Intermittent Mandatory Ventilation" with pressure support and pressure control, since a majority of trigger and cycling-off errors have a large spread. Enhancement of the graphics of FIG. 12 could be obtained by adding topographic descriptions of cumulated data points with similar coordinates by using 3-dimensional, color or other topographic representations.

Figure 13:
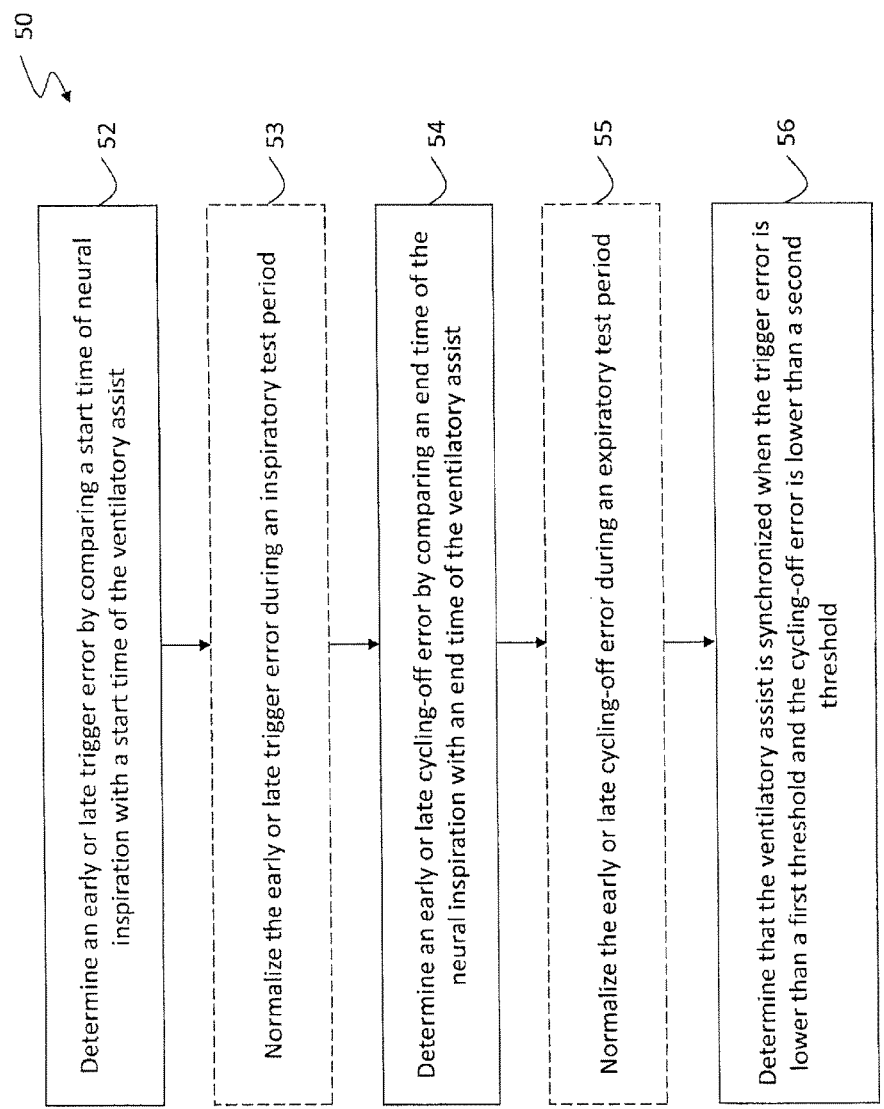
FIG. 13 is a flow chart showing operations of a method for quantifying timing discrepancies between inspiratory efforts and ventilatory assist according to an embodiment.

FIG. 13 is a flow chart showing operations of a method for quantifying timing discrepancies between inspiratory efforts and ventilatory assist according to an embodiment. A sequence 50 comprises operations that may be executed in varying order and not necessarily in the order as shown on FIG. 13. The sequence 50 comprises an operation 52 of determining a trigger error by comparing a start time of neural inspiration with a start time of the ventilatory assist, for example positive-pressure ventilatory assist. An early or late trigger error is determined by comparing a start time of neural inspiration with a start time of the ventilatory assist. As expressed hereinabove, the early or late trigger errors may be presented as absolute numbers as well as by logarithmic, exponential or power functions of these numbers. However, normalization of the early or late trigger error during an inspiratory test period may optionally take place at operation 53. Normalization of the early or late trigger errors involves expressing the early or late trigger errors as relative errors, including fractions or percentage, of the inspiratory test period. At operation 54, a cycling-off error may be determined by comparing an end time of the neural inspiration with an end time of the ventilatory assist. An early or late cycling-off error is determined by comparing an end time of the neural inspiration with an end time of the ventilatory assist. Normalization of the early or late cycling-off error during an expiratory test period may optionally take place at operation 55, in a similar manner as expressed hereinabove. It may then be determined, at operation 56, that the ventilatory assist is synchronized when the trigger error is lower than a first threshold and/or the cycling-off error is lower than a second threshold. Of course, the operations 52-56 can be performed using the features described in the foregoing disclosure.

Figure 14:
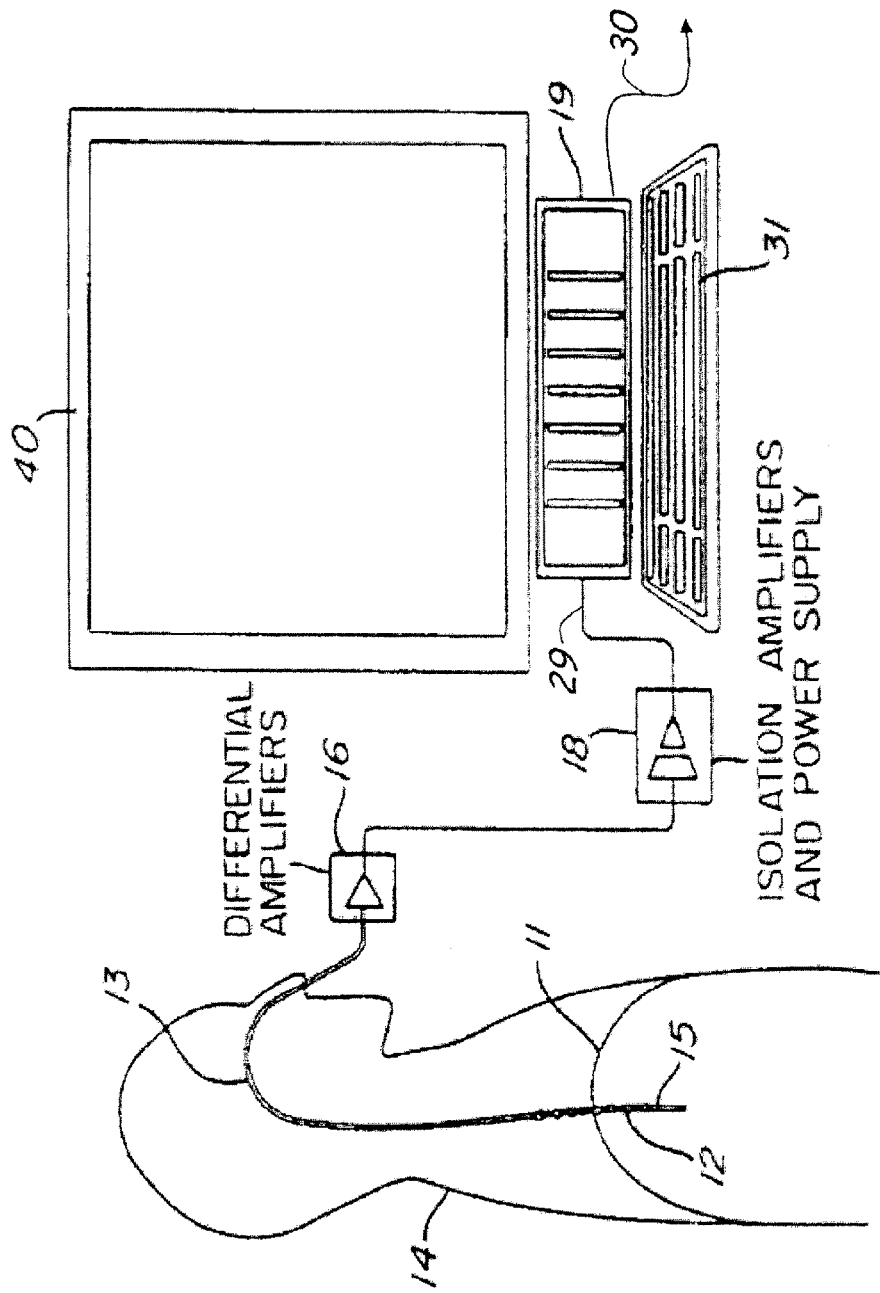
FIG. 14 is an example of system for carrying out into practice the method of FIG. 13.

FIG. 14 is a schematic diagram of a system for supporting the method of FIG. 13. Electrical activity (EAdi) of the diaphragm 11 of a human patient 14 is measured using an array of electrodes 12 mounted on the free end section 15 of an esophageal catheter 13 supporting the array of electrodes 12 as taught, for example, by the above mentioned U.S. Pat. No. 6,588,423 to Sinderby. The catheter 13 is introduced into the patient's esophagus through one nostril or the mouth until the array of electrodes 12 is situated at the level of the gastroesophageal junction. Electric wires (not shown) interconnect the electrodes with one or more differential amplifiers 16, providing one or more EAdi signals. Of course, other suitable methods and systems may be used to acquire EAdi signals.

The EAdi signals representing inspiratory efforts of the patient 14, possibly amplified by the differential amplifiers 16, are received at an interface 29 of a computer 19, possibly through one or more isolation amplifiers of a unit 18. The computer 19 also comprises a keyboard 31 for inputting commands and a display 40 for displaying information related to a patient's inspiratory effort and to ventilatory assist of the patient. Examples of information that the display 40 may show include, without limitation, EAdi tracings, Pvent tracings, trigger errors, cycling-off errors, inspiratory and expiratory test periods, and graphical representations of these errors. A particular graphical representation of trigger and cycling-off errors includes the above mentioned NeuroSync Index for patient-ventilator interaction. The computer 19 further comprises an interface 30 for connecting to a mechanical ventilator (not shown) and for receiving therefrom a state of the mechanical ventilator, a measurement signal reflecting a pressure, a flow or a volume of air supplied by the ventilator, or any other information related to the start time and end time of ventilatory assist.

The computer 19 comprises a processor (not explicitly shown) that may determine a trigger error by comparing a start time of neural inspiration, based on the EAdi signals, with a start time of the ventilatory assist, based on a state or measurement signal from the mechanical ventilator. The processor may also determine a cycling-off error by comparing an end time of the neural inspiration with an end time of the ventilatory assist, these parameters being also based, respectively, on the EAdi signals and on the state or measurement signal from the mechanical ventilator. The processor may then make a determination of a level of ventilatory assist synchrony based on a comparison of the trigger error with a first threshold, stored in a memory (not explicitly shown) of the computer 19, and/or on a comparison of the cycling-off error with a second threshold, also stored in the memory. The computer 19 may of course perform the above described operations over a plurality of breathing cycles of the patient 14. Consequently, the processor may calculate a ratio of occurrences of patient breaths when the ventilatory assist is synchronized over occurrences of patient breaths when the ventilatory assist is not synchronized.

In a particular aspect, the display 40 may provide a graphical presentation of the NeuroSync Index, which is a comprehensive asynchrony index for patient-ventilator interaction. The computer may provide, for each breathing cycle of the patient 14, a trigger error value and a cycling-off error value for plotting at the display 40 a graph according to the formats shown on FIGS. 8-12.

Experimental Protocol

An experimental protocol was defined to validate an automated and standardized process for quantifying and displaying patient-ventilator interaction. Using available data from mechanically ventilated patients, patient-ventilator interaction was evaluated from waveforms of airway pressure and diaphragm electrical activity. A new standardized and automated index of patient-ventilator interaction, the NeuroSync Index, was validated and compared to manual analysis and previously published indices.

Index validation was carried out in Hospital Laboratory, data collection in adult intensive care unit (ICU). 24 patients with acute respiratory failure of varied etiology receiving pressure support ventilation.

The EAdi and ventilator pressure waveforms were analyzed with automated processes that detect ventilator and EAdi timings and quantify any error therebetween. A comparison of manual and automated detection methods was used to produce high test-retest and inter-rater reliability. The NeuroSync Index increased the sensitivity of detecting dyssynchronies, compared to earlier indices, which were found to only detect severe asynchronies.

The foregoing will show that the NeuroSync Index introduces an automated method to determine patient-ventilator interaction with higher accuracy than conventional methods. A graphical display allows a rapid overview of patient-ventilator interaction and breathing pattern.

Patient-ventilator interaction describes how well matched the respirator is to the timing of breathing of the patient. Today, most ventilators offer patient-triggered modes, with the promise that they are "synchronized" to patient effort, in the sense that the ventilator initiates ventilatory assist at the onset of an inspiration and terminates the assist when inspiration ends. Despite this claim, the prevalence of severe patient-ventilator asynchrony can be as high as 25% in patients with acute respiratory failure. As is well-known, severe patient-ventilator asynchrony is associated with adverse effects, such as prolonged time on mechanical ventilation and increased use of sedation.

The most common method for evaluating patient-ventilator asynchrony is interpretation of airway pressure and flow waveforms. However, such a method underestimates considerably the prevalence of the most severe asynchronies and may even fail to reveal whether the patient is breathing or not. Thus, there was need for a more reliable and validated index of patient-ventilator interaction, quantifying in a standardized fashion the magnitude of error that the ventilatory assist deviates from its targets for triggering and cycling-off.

It is generally agreed that the diaphragm electrical activity (EAdi) waveform is a reliable signal to determine the patient's neural respiratory drive as well as patient-ventilator interaction. The present study introduces a new method based on the measurements of EAdi and airway pressure to automatically detect, quantify, and display patient-ventilator interaction.

Data sets used in the present study, including 43 data sets in total, were obtained from previously published material. The data sets were obtained from 24 adult patients with acute respiratory failure of varying etiology, on pressure support ventilation. Each patient had the placement of an esophageal catheter for recordings of EAdi waveforms. EAdi was measured in conjunction with ventilator pressure (Pvent) and flow waveforms, over 5-minute periods. Data sets were analyzed automatically with processes described below. An automatic analysis was validated by a manual analysis.

Manual Analysis: Detection of Neural (EAdi) and Ventilator Time Points

Two (2) expert analysts with over one (1) year of almost daily experience analyzed all data sets twice. The manual analysis was performed with a visual display of the EAdi, Pvent, and flow waveforms, and the placement of time cursors.

Automatic Analysis: Detection of Neural (EAdi) and Ventilator Time Points

Automatic computer processes were designed to detect the onset and end of each neural inspiration, and the onset and end of each ventilator cycle.

Figure 15A:
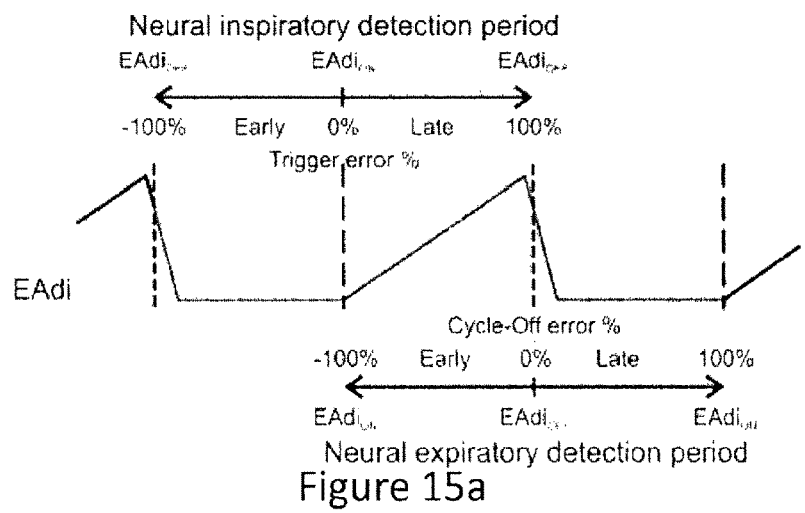
FIG. 15a is a diagram showing an EAdi signal with its indicators for onset ($EAdi_{ON}$) and termination ($EAdi_{OFF}$)
Figure 15B:
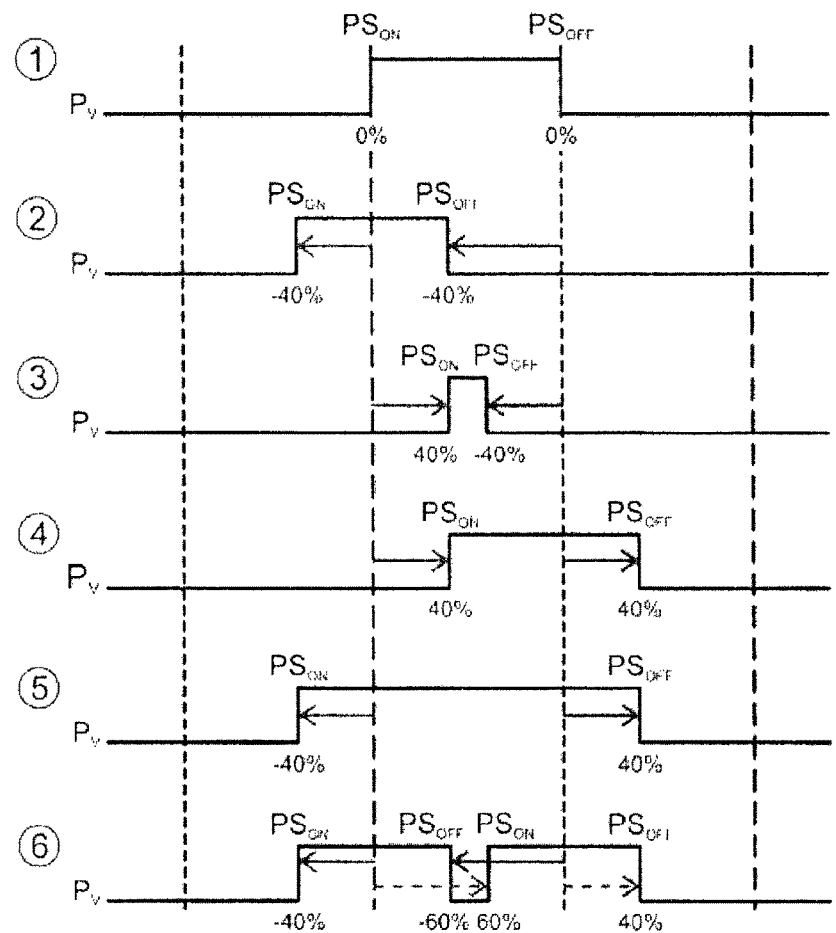
FIG. 15b is a diagram showing examples of synchrony, dyssynchrony, and asynchrony between pressure support and neural activity.
Figure 15C:
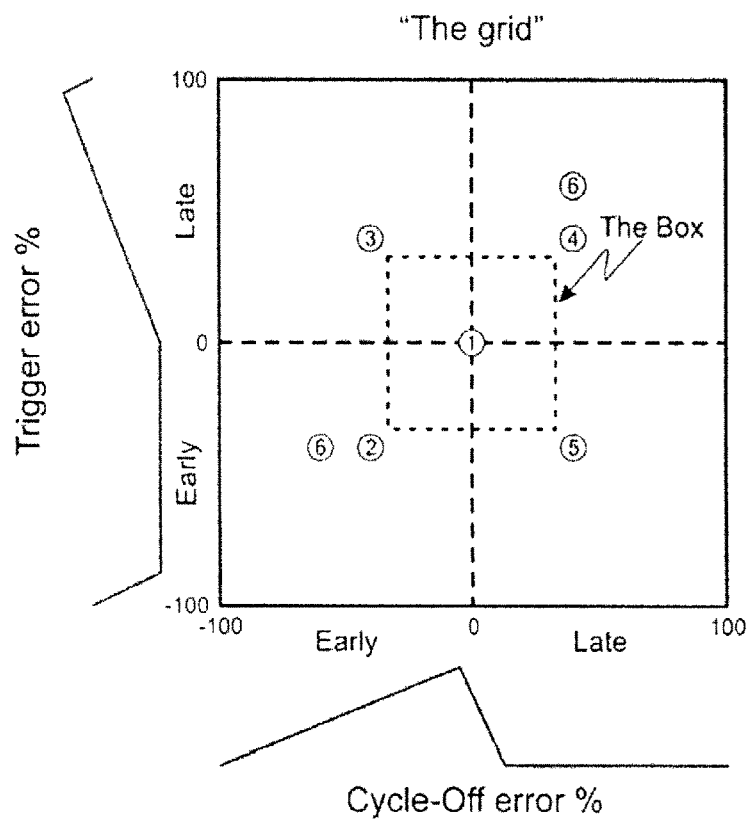
FIG. 15c is a graphical representation of the NeuroSync Index.
Figure 15D:
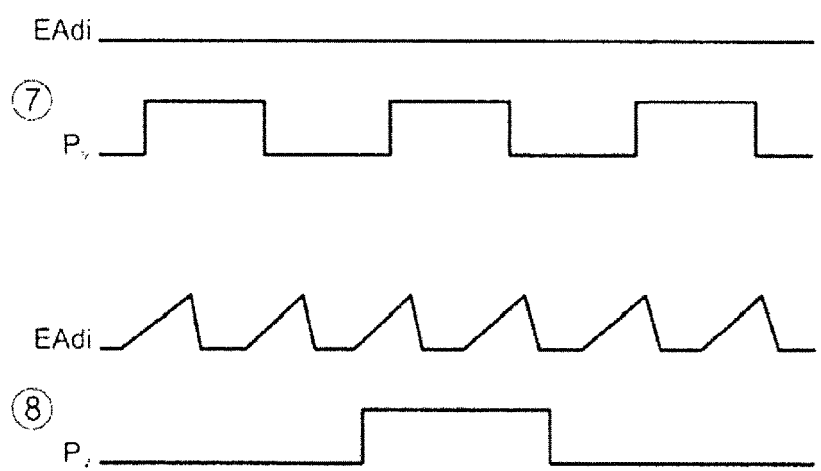
FIG. 15d is a diagram showing additional examples of extreme asynchrony between pressure support and neural activity.

FIGS. 15a-15d provide a schematic description of the NeuroSync Index. Specifically, FIG. 15a is a diagram showing an EAdi signal with its indicators for onset ($EAdi_{ON}$) and termination ($EAdi_{OFF}$). Possible ranges of "trigger error" expressed in % relative to $EAdi_{ON}$ and $EAdi_{OFF}$ during the "neural inspiratory detection period" as well as range for "cycle-off error" expressed in % relative to $EAdi_{ON}$ and $EAdi_{OFF}$ during the "neural expiratory detection period" are shown. FIG. 15b is a diagram showing examples of synchrony, dyssynchrony, and asynchrony between pressure support and neural activity. These examples show possible combinations of trigger errors, in the form of relative errors between $EADI_{ON}$ and $PS_{ON}$ as well as $EADI_{OFF}$ and $PS_{OFF}$. FIG. 15c is a graphical representation of the NeuroSync Index. The examples of FIG. 15b are located in a grid of FIG. 15c. FIG. 15d is a diagram showing additional examples of extreme asynchrony between pressure support and neural activity. Included on FIG. 15d are an example of assist without EAdi and an example of multiple EAdi with or without assist.

Automatic detection of the onset of EAdi, at the beginning of neural inspiration, was obtained by detecting increases in EAdi, starting from the nadir of the EAdi. When a preset increase in EAdi (the EAdi trigger level) was reached, the time at the nadir was stored ("onset of EAdi", $EAdi_{ON}$, illustrated as a long-dashed vertical line on FIG. 15a). The amplitude at $EAdi_{ON}$ was also stored. Three trigger levels were applied: 0.25, 0.5 and 1.0 pV. The end of EAdi (beginning of neural expiration) was automatically detected by finding when the EAdi had decreased by 30% from its peak (the EAdi termination level), and this was stored as the end of EAdi ($EAdi_{OFF}$, illustrated as short dashed vertical lines on FIG. 15a). If the peak signal was less than 2 µV, the required percentage decrease from the peak value was linearly increased from 30% to 70%, until a value of 1 µV.

The onset of ventilator assist was determined from the ventilator pressure (Pvent) waveform. In this case, the onset of pressure support ($PS_{ON}$) was automatically detected by searching for an increase in pressure of more than 3 cm $H_2O$; when reached, the time value obtained at the nadir was stored as $PS_{ON}$ (examples 1-6 shown on FIG. 15b). The termination of pressure support ($PS_{OFF}$, examples 1-6 shown on FIG. 15b) was automatically detected by searching for a decrease in pressure by 30% from its peak.

Description of Neural Index to Evaluate Patient-Ventilator Interaction ("NeuroSync Index")

The NeuroSync Index was calculated for the data sets using both a manual method ($NeuroSync_{MANU}$) and an automated method ($NeuroSync_{AUTO}$) for determining EAdi and Pvent timings. Note that $NeuroSync_{AUTO}$ was repeated for trigger levels of 0.25, 0.5 and 1.0 µV.

First, for each EAdi effort, a neural inspiratory and expiratory detection period was determined and divided into early and late segments (FIG. 15a). Early and late segments were normalized to express relative values ranging from −100% to 0% to +100%.

A graphical presentation of the NeuroSync Index is shown on FIG. 15c, subsequently referred to as the "grid". The grid represents the neural inspiratory (vertical axis) and expiratory detection (horizontal axis) periods and also has a "box" to indicate limits between acceptable synchrony (neural efforts that relate well to ventilatory assist), dyssynchrony (neural efforts poorly related to ventilatory assist), and asynchrony (neural efforts not related to ventilatory assist or vice versa).

In the present study "synchrony" was defined as events that land inside-the-box and that have less than ±33% difference between $EAdi_{ON}$ and $PS_{ON}$ as well as $EAdi_{OFF}$ and $PS_{OFF}$, respectively. Events landing outside-the-box but on-the-grid were defined as "dyssynchrony". Events that land off-the-grid were defined as "asynchrony". Examples of synchrony, dyssynchrony, and asynchrony are described below. Referring at once to FIGS. 15b and 15c, the following Examples 1-6 are illustrated:

Example 1

A ventilator breath delivered in synchrony with EAdi: $EAdi_{ON}$ and $PS_{ON}$ as well as $EAdi_{OFF}$ and $PS_{OFF}$ occur simultaneously. Events appear on-the-grid and inside-the-box.

Example 2

Early triggering ($PS_{ON}$ occurs −40% early relative to $EAdi_{ON}$) and early cycling-off ($PS_{OFF}$ −40% early relative to $EAdi_{OFF}$). Events appear outside-the-box (dyssynchrony) in the lower left quadrant of the grid.

Example 3

Late triggering ($PS_{ON}$ occurs 40% late relative to $EAdi_{ON}$) and early cycling-off ($PS_{OFF}$ −40% early relative to $EAdi_{OFF}$). Events appear outside-the-box in the upper left quadrant of the grid.

Example 4

Late triggering ($PS_{ON}$ occur 40% late relative to $EAdi_{ON}$) and late cycling-off ($PS_{OFF}$ 40% late relative to $EAdi_{OFF}$). Events appear outside-the-box in the upper right quadrant of the grid.

Example 5

Early triggering ($PS_{ON}$ occur −40% early relative to $EAdi_{ON}$) and late cycling-off ($PS_{OFF}$ 40% late relative to $EAdi_{OFF}$). Events appear outside-the-box in the lower right quadrant of the grid.

Example 6

Multiple assist with EAdi (Double-triggering). First PS: Early triggering ($PS_{ON}$ occur −40% early relative to $EAdi_{ON}$) and early cycling-off ($PS_{OFF}$ −40% early relative to $EAdi_{OFF}$), land outside-the-box in the lower left quadrant of the grid (same as example 2). Second PS: Late triggering ($PS_{ON}$ occur 40% late relative to $EAdi_{ON}$) and late cycling-off ($PS_{OFF}$ 40% late relative to $EAdi_{OFF}$) land outside-the-box in the upper right quadrant of the grid (same as example 4).

FIG. 15d shows two (2) additional examples of extreme asynchrony that fall off-the-grid and are given a value of 100% for the NeuroSync Index. Example 7 exemplifies assist without EAdi (sometimes known as "auto-triggering"). Example 8 illustrates EAdi without assist (also known as "wasted effort") and multiple EAdi with one assist.

To numerically quantify the NeuroSync Index, absolute values for trigger and cycling-off errors were used. Also, events falling "inside-the-box" (acceptable synchrony), "outside-the-box" (dyssynchrony), as well as values falling "off-the-grid" (asynchrony) were counted and presented their relative proportions.

Defragmentation

To evaluate the influence of sub-ventilatory efforts, data was also processed with a defragmentation method, ignoring EAdi triggered breaths of less than 0.15 µV and pressure detected breaths of less than 1.5 cm $H_2O$.

Comparison of Indices

The $NeuroSync_{MANU}$ and $NeuroSynd_{AUTO}$ indices were compared to an asynchrony index, referred to herein as $AI_{Colombo}$, published by Colombo et al., (Colombo D, Cammarota G, Alemani M, et al. Efficacy of ventilator waveforms observation in detecting patient-ventilator asynchrony. *Crit Care Med.* 2011 November; 39(11):2452-7). In Colombo et al., three (3) examiners with specific expertise in patient-ventilator interaction used the EAdi signal to verify the accuracy of flow-pressure waveform analysis, referred to as $AI_{Thille}$, described by Thille et al. (Thille A W, Rodriguez P, Cabello B, et al. Patient-ventilator asynchrony during assisted mechanical ventilation. *Intensive Care Med.* 2006; 32(10): 1515-22).

Neural (breathing) frequency ($f_N$) was calculated from the EAdi signal. Ventilator frequency ($f_{Vent}$) was calculated from $P_V$.

Statistics

Intraclass correlation coefficient (ICC) was used for test-retest and inter-rater reliability. Linear regression analysis was used to determine regression coefficients, intercepts, and determination coefficients. Unpaired comparisons were made with Mann-Whitney rank sum test.

Results

Reliability of Automated Analysis

For each data set analysis, the two (2) expert analysts manually detected and assigned on average 4562 (range 4439-4686) events according to the classifications given in the foregoing description of FIGS. 15a-15d. Test-retest reliability and inter-rater reliability was expressed by ICCs for the NeuroSync Index obtained by the expert analysts during two repeated analyses, as recited in Table 1. In the Table, results marked with an asterisk identify test and retest for the same examiner. The lowest ICC for reproducibility was 0.97 and lowest ICC value obtained when comparing the two expert analysts was 0.94.

TABLE 1

Intraclass correlation coefficients for NeuroSync Index obtained by examiners 1 and 2 during their $1^{st}$ and $2^{nd}$ manual analysis.

| | | Examiner 2 | | Examiner 1 |
|---|---|---|---|---|
| | | $1^{st}$ Analysis | $2^{nd}$ Analysis | $2^{nd}$ Analysis |
| Examiner 1 | $1^{st}$ Analysis | 0.94 | 0.96 | 0.99* |
| | $2^{nd}$ Analysis | 0.95 | 0.97 | |
| Examiner 2 | $2^{nd}$ Analysis | 0.97* | | |

Figures 16A, 16B:
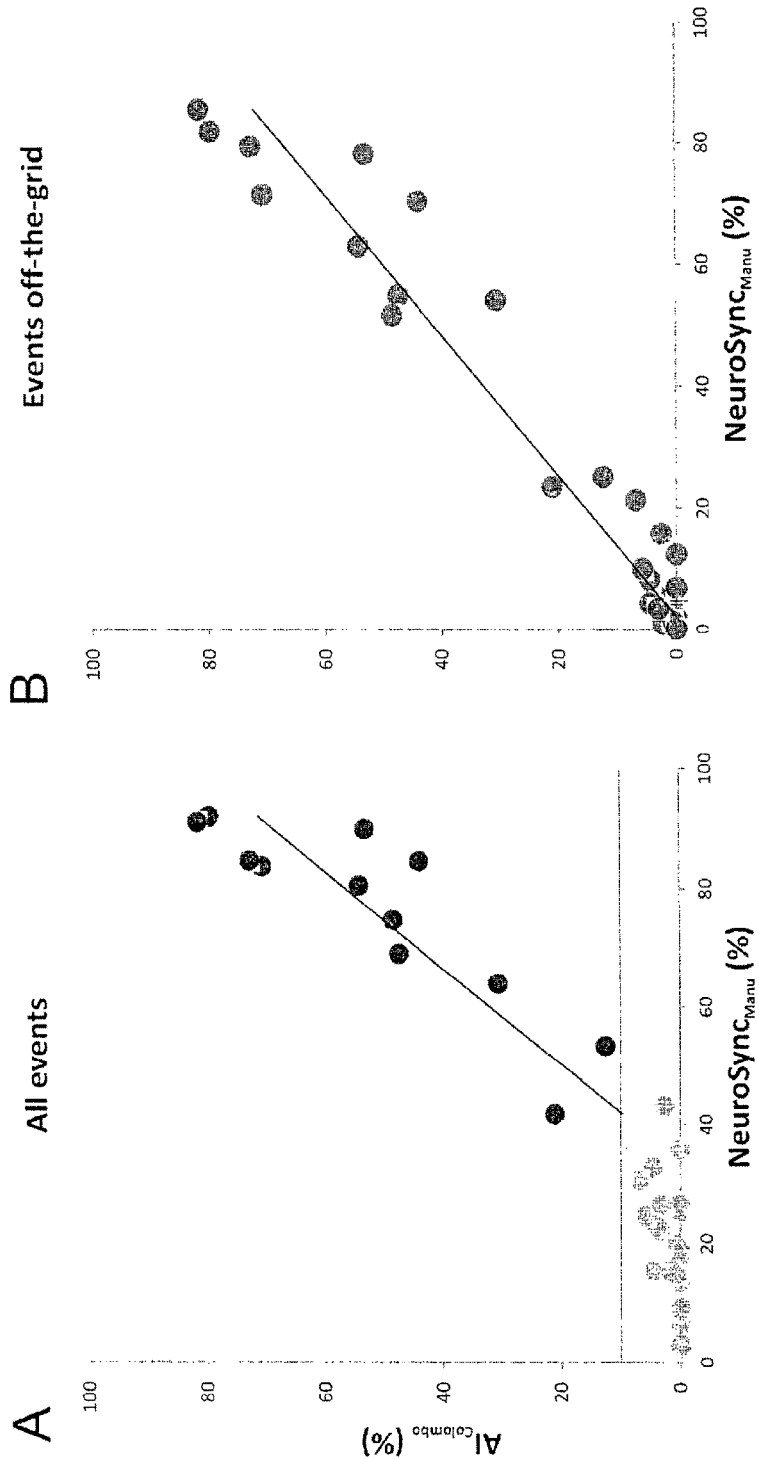
FIG. 16A is a graph illustrating a relationship between a value $AI_{Colombo}$ versus a value $NeuroSync_{MANU}$.
FIG. 16B is a graph illustrating the same relationship as in FIG. 16A, with only "off-the-grid" breaths (asynchrony only)

FIG. 16A is a graph illustrating a relationship between a value $AI_{Colombo}$ versus a value $NeuroSync_{MANU}$. Note that as $NeuroSync_{MANU}$ increases (i.e. detecting more asynchrony and dyssynchrony) towards 40%, $AI_{Colombo}$ remains consistently at a low value, after which the two increase in proportion. The ICC between $AI_{colomb}$ and $NeuroSync_{MANU}$ for all data where the $AI_{Colombo}$ exceeds 10% was 0.87. FIG. 16B is a graph illustrating the same relationship as in FIG. 16A, with only "off-the-grid" breaths (asynchrony only). Illustrated NeuroSync Index and $AI_{Colombo}$ results were obtained manually by expert analysts verifying onset and termination of inspiratory efforts by EAdi.

Table 2 provides ICCs between the $NeuroSync_{MANU}$ and $NeuroSync_{AUTO}$ indices at different trigger levels, and with and without defragmentation. In Table 2, "defrag" denotes an automated analysis excluding EAdi detected breaths of less than 0.15 µV and pressure deflection trigger of 3.0 cm $H_2O$, ignoring pressure detected breaths of less than 1.5 cm $H_2O$.

TABLE 2

Intraclass Correlation Coefficients for NeuroSync Index obtained between manual analyses (mean of all 4 analyses performed by examiner 1 and 2) and automated detection with trigger thresholds of 0.25, 0.50, and 1.00 µV.

| | | Manual Analysis (mean of all analyses) |
|---|---|---|
| Automatic analysis | Trigger level (µV) 0.25 | 0.91 |
| | | 0.99 defrag |
| | 0.50 | 0.97 |
| | | 0.95 defrag |
| | 1.00 | 0.90 |
| | | 0.88 defrag |

Figure 17:
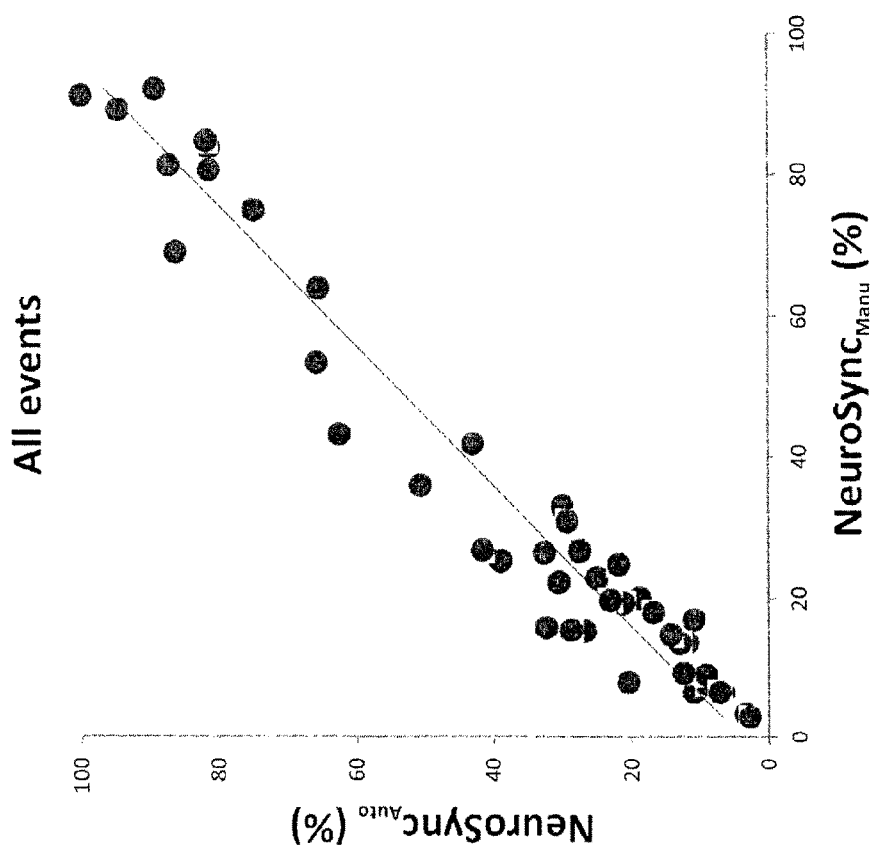
FIG. 17 shows a relationship between the value $NeuroSync_{MANU}$ and a value $NeuroSync_{AUTO}$ with 0.5 μV trigger.

FIG. 17 shows a relationship between the value $NeuroSync_{MANU}$ and a value $NeuroSync_{AUTO}$ with 0.5 µV trigger. Excellent correlation may be observed between manual an automated methods for determining EAdi and Pvent timings.

Graphical Display

Figure 18A:
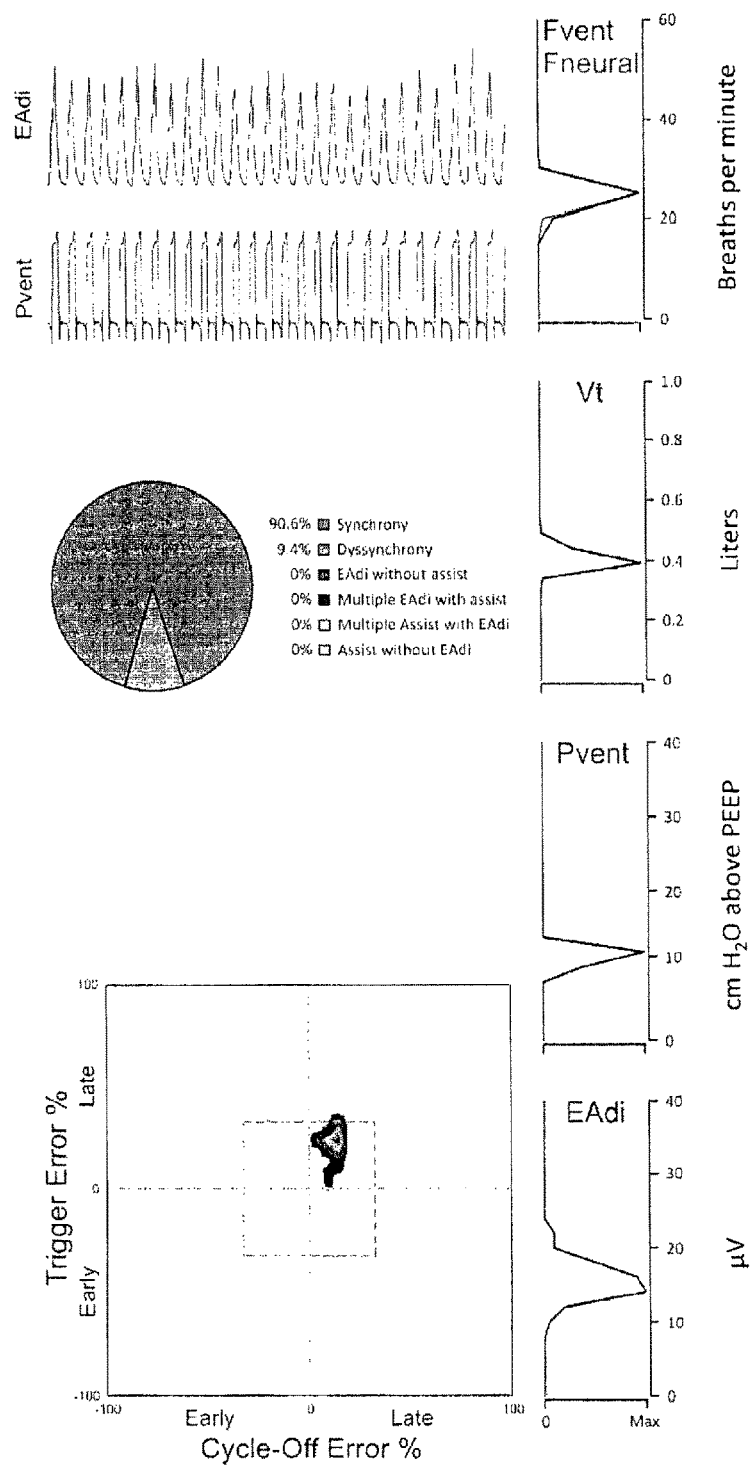
FIGS. 18a, 18b and 18c are diagrams providing examples of ventilation and EAdi waveforms, with synchrony analysis, in three (3) different patients having distinct breathing patterns.
Figure 18B:
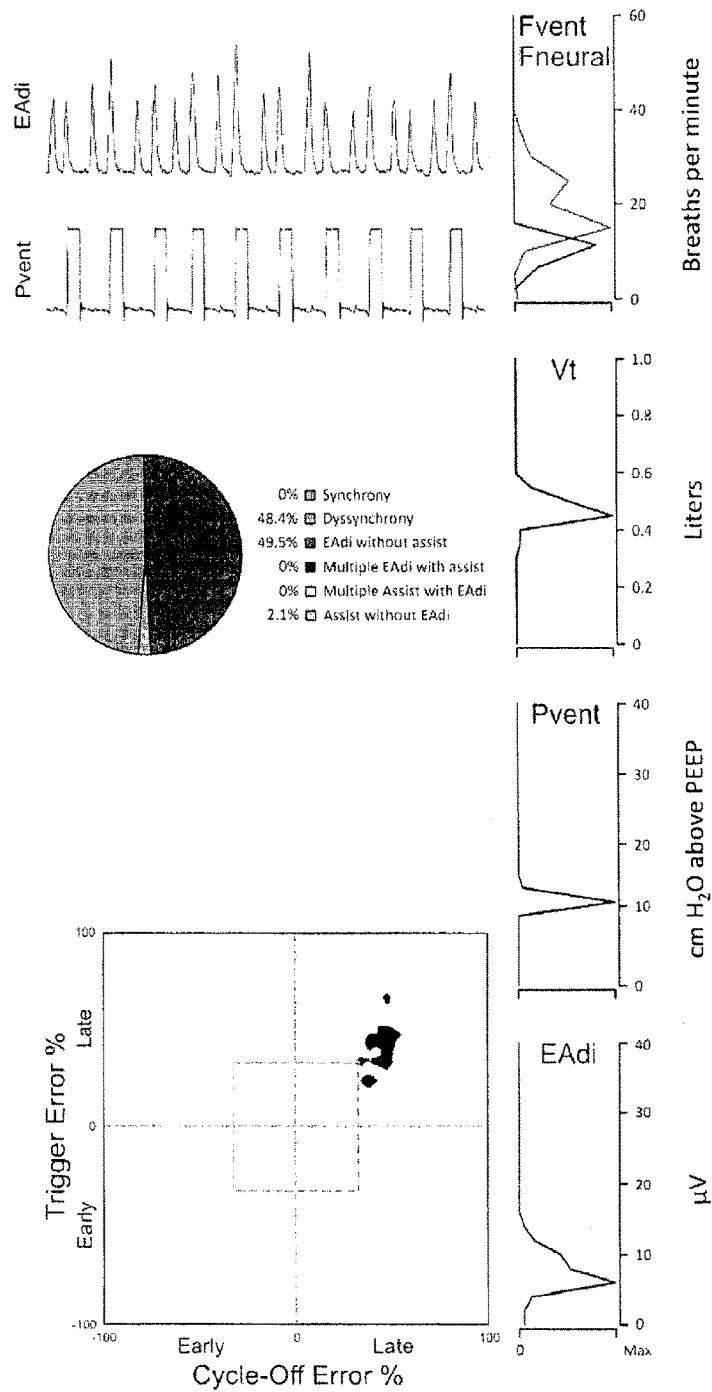
Figure 18C:
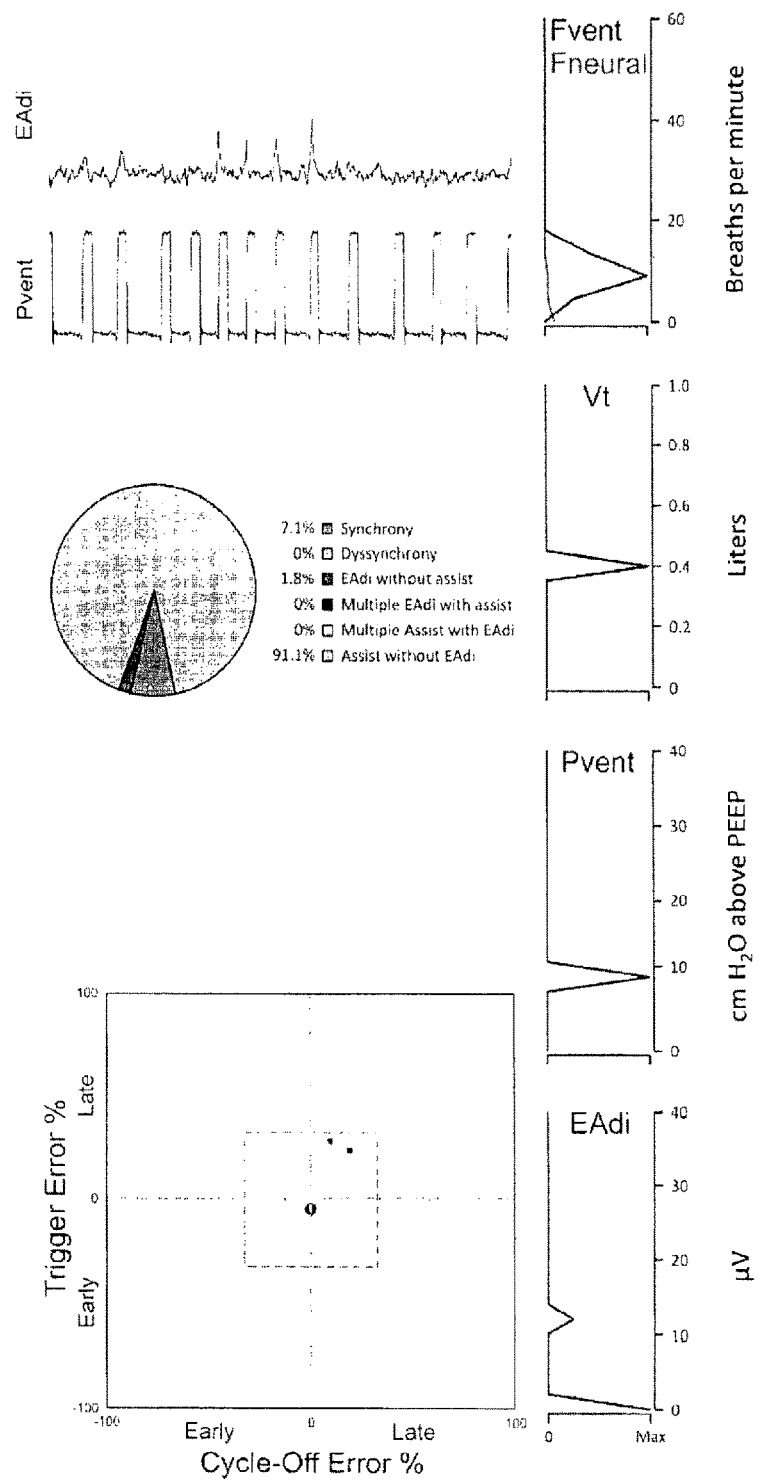

FIGS. 18a, 18b and 18c are diagrams providing examples of ventilation and EAdi waveforms, with synchrony analysis, in three (3) different patients having distinct breathing patterns. Each of FIGS. 18a-18c comprises raw EAdi and Pvent tracings, in a top left section, a pie-diagram showing distribution of breaths between synchronicity, between EAdi and Pvent, and various types of asynchronicity, in a middle left section, and a NeuroSync grid, in a bottom left section. The NeuroSync grid displays intra-breath patient-ventilator interaction with synchrony (inside-the-box) and dyssynchrony (outside-the-box). Each of these Figures also comprises a right column comprising, from top to bottom, histograms of (i) ventilator and neural respiratory rate, in breaths per minute, (ii) tidal volumes, in liters, (iii) ventilator pressure above positive end-expiratory pressure (PEEP), in cm $H_2O$, and (iv) EAdi, in µV. A horizontal axis on all histograms has a range from zero (0) to a maximum number of occurrences for the illustrated quantity.

FIG. 18a demonstrates an example of good patient-ventilator interaction. The raw tracings in the top panel show clearly distinguishable EAdi and $P_V$ waveforms. The pie-diagram shows that almost all breaths (close to 91%) are synchronous. Using the grid analysis, it can be seen that the majority of signals appear inside-the-box in the upper right quadrant, indicating synchronized assist with a slightly delayed onset and termination of assist relative to the EAdi. The histograms (top to bottom on right side) show that $f_{Vent}$ and $f_N$ are stable between 20-25 breaths/min. Tidal volume was 0.4-0.5 liter at an assist level of 12-14 cm $H_2O$ above PEEP. EAdi is concentrated in the range of 15-20 µV.

FIG. 18B depicts an example of poor patient-ventilator interaction. The EAdi and $P_V$ waveforms are distinguishable, but it is clear that neural efforts occur more frequently than ventilator breaths. The pie-diagram reveals 50% of the EAdi breaths were not assisted, and 2% of assist occurred without EAdi. 48% of the signals appear on-the-grid in the upper right quadrant outside-the-box indicating substantial delays for both onset and termination of assist relative to EAdi. The histograms show that $f_{Vent}$ occurs at 5-15 breaths/min whereas $f_N$ demonstrates two peaks at 10 and 35 breaths/minute. Tidal volume is 0.4-0.6 l at an assist level of 12-14 cm $H_2O$ above PEEP. EAdi ranges 5-20 µV.

FIG. 18C illustrates another case of poor patient-ventilator interaction. The waveforms show that EAdi is infrequent and almost non-distinguishable whereas $P_{vent}$ is clearly distinguishable and frequent. The pie-diagram indicates a 91% of assist without EAdi, 2% of EAdi without assist and only 7% of breaths land inside-the-box on-the-grid. The histograms show that $f_{Vent}$ is stable at 14-16 breaths/min whereas $f_N$ is either very low (few breaths) or very high (>60 breaths/min). Tidal volume is 0.3-0.4 l at an assist level of 12-14 cm $H_2O$ above PEEP. EAdi shows that some breaths reach 12-14 µV, but the majority is lower than 2 µV.

Subventilatory Efforts 61 percent of the analyzed data sets had two (2) or fewer subventilatory EAdi efforts per minute and only 6% had more than eight (8) subventilatory EAdi efforts per minute. The EAdi was higher (P=0.019) for data sets that had two (2) or fewer subventilatory EAdi efforts per minute (5.7 µV, n=26) compared to those with more than two (2) subventilatory EAdi efforts per minute (3.0 µV, n=17).

With respect to frequency of breaths, as depicted in Table 3, the ICCs between $f_N$ with automated and manual analysis were poor for breaths with EAdi amplitudes lower than 1 μV and excellent above 2 μV. Comparison of $f_{Vent}$ between automated and manual analysis for defragmented breaths resulted in an ICC of 1.0. In Table 3, "Defrag" denotes automated analysis with EAdi trigger of 0.5 μV excluding EAdi detected breaths of less than 0.15 μV and pressure deflection trigger of 3.0 cm H$_2$O ignoring pressure detected breaths of less than 1.5 cm H$_2$O s. Determination coefficients were obtained for all subjects, and after exclusion of subjects with diaphragm electrical activity deflections (ΔEAdi) equal to or below 1 or 2 μV, respectively.

TABLE 3

ICCs for neural (breathing) frequency ($f_N$) between manual (mean of 4 analyzes) and automatic analyzes with and without sub-ventilatory effort defragmentation.

| | ΔEAdi | $f_N$, automated analysis (0.5 μV + defrag) |
|---|---|---|
| $f_N$, manual analysis | All subjects | 0.62 |
| | Excluding EAdi ≤ 1 μV | 0.83 |
| | Excluding EAdi ≤ 2 μV | 0.96 |

Discussion

The present study introduces a new method for automated quantification and graphical presentation of patient-ventilator interaction and breathing pattern, using the EAdi waveform as the reference.

On-the-Grid (Synchrony/Dyssynchrony)

The NeuroSync Index—in combination with the graphical illustration of the grid—allows an understanding of the relative differences in timing between neural efforts and ventilatory assist. The index, therefore, becomes insensitive to variances in breathing pattern which can occur with age and disease. For example, a trigger delay of 100 ms in a newborn having a neural inspiratory time of 300 ms results in a 33% error, and could be considered unacceptable. However, in an adult patient with a neural inspiratory time of 800 ms, the trigger delay represents a 12% error. Hence, the relative limits chosen to differentiate between synchrony and dyssynchrony can be the same regardless of age and disability.

Thine et al., mentioned hereinabove, were first to describe and quantify major asynchronies, such as wasted efforts and auto-triggering, using only airway pressure and flow waveforms, albeit without the EAdi as a reference. To describe dyssynchrony, the method of Thille et al. involved detection of "short" and "prolonged" cycles. Considering the natural variability in breathing, however, it has been reported that the significance of detecting these remains unclear. The closest comparison to the NeuroSync Index for "short cycles" would be late triggering and early cycling-off values which, upon looking at the grid, would fall outside-the-box i.e. upper left quadrant of the grid. "Long cycles" are likely to be associated with early trigger (lower quadrants) and/or delayed cycling-off (right side quadrants) or repeated EAdi during assist (off-the-grid).

The AI$_{Thille}$ index also includes "double-triggering", an event corresponding to "multiple-assist-during-EAdi" with the NeuroSync Index. Multiple-assist-during-EAdi reflects repeated trigger and cycling-off errors during the same neural effort which graphically places these events on-the-grid. It should be noted that in assist-volume control, double-triggering is a severe asynchrony associated with excessive tidal volumes. In non-flow and volume regulated modes, double triggering would only cause a timing error with a short interruption of the inspiratory assist during an inspiratory effort.

Although the AI$_{Thille}$ has some ability to detect intra-breath mismatch between inspiratory effort and ventilatory assist, our results show that the AI$_{Thille}$-even when verified by EAdi—was insensitive relative to the NeuroSync Index. This is evidenced in FIG. 16a showing that the NeuroSync Index reached 40% asynchrony before AI$_{Colombo}$ surpassed 10% asynchrony. The close association between indices when AI$_{Colombo}$ exceeds 10% (FIG. 16a) shows that asynchronies are detected by both indices. As evidenced by a close relationship between the "off-the-grid" events detected with the NeuroSync Index and AI$_{Colombo}$, most asynchronies that appear "off-the-grid" with the NeuroSync Index provide information similar to that of the pressure and flow based asynchrony index described by Thille et al.

Another index of asynchrony based on EAdi was described by Beck et al. (Beck J, Tucci M, Emeriaud G, Lacroix J, Sinderby C. Prolonged neural expiratory time induced by mechanical ventilation in infants. *Pediatr Res.* 2004 May; 55(5):747-54), where the sum of trigger delays and cycling-off delays (determined manually) were expressed as a percentage of the total neural respiratory cycle. The NeuroSync Index can be considered a development of the previously described EAdi-based index.

Off-the-Grid (Asynchrony)

The NeuroSync event defined as "EAdi-without-assist" corresponds to "ineffective triggering" with the AI$_{Thille}$. An inspiratory effort not rewarded by a ventilator breath is a failure for a "triggered" mode and is the asynchrony predominantly associated with adverse patient outcomes. As "ineffective triggering" typically relates to a failure of the conventional ventilator's flow and pressure sensors to detect an inspiratory effort, it is not surprising that the prevalence of ineffective triggering is greatly underestimated by flow airway and pressure detection.

The NeuroSync event defined as "Assist-without-EAdi" resembles "auto-triggering" with AI$_{Thille}$. If not induced by backup modes during apnea, auto-triggering is another faulty condition where the ventilator triggers and cycles-off uncontrollably and hyperventilates the patient. "Auto-triggering" is a very difficult asynchrony to detect with AI$_{Thille}$, since there is no true patient reference to validate the ventilator's triggering, Sinderby et al. (Sinderby C, Beck J. Proportional assist ventilation and neurally adjusted ventilatory assist—better approaches to patient ventilator synchrony. *Clin Chest Med.* 2008 June; 29(2):329-42).

The NeuroSync Index also introduces another type of asynchrony labeled "multiple-EAdi-during-assist", a severe type of asynchrony where the ventilator is delivering several breaths for one neural inspiratory effort. The AI$_{Thille}$ has no counterpart for "multiple-EAdi-during-assist".

Since, "EAdi-without-assist", "Assist without EAdi", and "Multiple-EAdi-during-assist" all describe failures of the ventilator trigger and cycling-off functions, these events were labeled as 100% trigger error and 100% cycling-off error, which graphically places them off-the-grid, and labeled as asynchrony.

In the context of the above discussion it is important to note that AI$_{Colombo}$ significantly increases the sensitivity to detect asynchrony compared to AI$_{Thille}$.

Critique on the NeuroSync Index

A neural inspiratory effort modulates motor-unit firing rate and recruitment of the diaphragm, whose temporo-spatial summation yields the EAdi. Hence, the EAdi signal if acquired and processed accurately represents the neural inspiratory drive to the diaphragm. The present study uses a recommended and standardized method to process EAdi. Yet, as expressed hereinabove, EAdi can be disturbed by other signals such as the ECG, thus impairing accurate determination of the onset and/or end of a neural effort. In the present EAdi analysis, the maximum error determination of the onset and end of a single neural is estimated to be equivalent to the duration of P-waveforms or QRS-waveforms. When averaged over hundreds of breaths, this error would become minute.

Strong ICCs for test-retest, inter-rater, and inter-method reliability suggest that the NeuroSync Index and automated detection method are both valid and reliable. The large amount of identified events per analysis (average n=4562) supports good test-retest reliability during the manual analysis.

A problem of subventilatory EAdi efforts is that if they fail to initiate assist the event is classified as EAdi-without-assist (ineffective effort) whereas if assist is initiated it is classified as assist-without-EAdi (auto-triggering). Also, subventilatory EAdi efforts introduce uncertainties in determining neural breathing pattern. Our analysis showed that subventilatory efforts are rare and typically related to very low EAdi amplitudes (<2-3 µV) and that their elimination has its greatest value at sensitive trigger levels (0.25 µV). This underlines the importance of a good signal to noise ratio for this type of automated analysis.

With regards to the agreement between manual and automated analysis to determine $f_N$, it was clear that low EAdi amplitude worsened the reliability. Note that although the agreement for manual and automated (defragmented) analysis to determine $f_{Vent}$ was perfect, this does not imply good patient-ventilator synchrony only that automated detection of pressure waveforms can be reliable.

Conclusion Regarding the Experimental Results

The NeuroSync Index introduces an automated method to determine patient-ventilatory asynchrony with higher accuracy than previous methods. A graphical display allows a rapid overview of patient-ventilator interaction and breathing pattern.

Closing

Those of ordinary skill in the art will realize that the description of the method and system for quantifying timing discrepancies between inspiratory efforts and ventilatory assist are illustrative only and are not intended to be in any way limiting. Other embodiments will readily suggest themselves to such persons with ordinary skill in the art having the benefit of the present disclosure. Furthermore, the disclosed method and system may be customized to offer valuable solutions to existing needs and problems of providing ventilatory assist to patients.

In the interest of clarity, not all of the routine features of the implementations of the method and system for quantifying timing discrepancies between inspiratory efforts and ventilatory assist are shown and described. It will, of course, be appreciated that in the development of any such actual implementation of the method or of the system, numerous implementation-specific decisions may need to be made in order to achieve the developer's specific goals, such as compliance with application-, system-, and business-related constraints, and that these specific goals will vary from one implementation to another and from one developer to another. Moreover, it will be appreciated that a development effort might be complex and time-consuming, but would nevertheless be a routine undertaking of engineering for those of ordinary skill in the field having the benefit of the present disclosure.

In accordance with the present disclosure, the process operations, described herein may be implemented using various types of operating systems, computing platforms, network devices, computer programs, and/or general purpose machines. In addition, those of ordinary skill in the art will recognize that devices of a less general purpose nature, such as hardwired devices, field programmable gate arrays (FPGAs), application specific integrated circuits (ASICs), or the like, may also be used. Where a method comprising a series of process operations is implemented by a computer or a machine and those process operations may be stored as a series of instructions readable by the machine, they may be stored on a tangible medium.

Although the present disclosure has been described hereinabove by way of non-restrictive, illustrative embodiments thereof, these embodiments may be modified at will within the scope of the appended claims without departing from the spirit and nature of the present disclosure.

What is claimed is:

1. A method of adjusting a ventilatory support system based on timing discrepancies between a patient's inspiratory effort and ventilatory assist to the patient, comprising:

receiving, at the ventilatory support system, from one or more electrodes, a neural inspiration signal representing an inspiratory effort of the patient;

receiving, at the ventilatory support system, from a mechanical ventilator providing the ventilatory assist to the patient, a measurement signal representing a start time and an end time of the ventilatory assist;

determining, based on the neural inspiration signal, a trigger error by comparing a start time of a current inspiratory effort of the patient with the start time of the ventilatory assist, wherein determining the trigger error comprises ignoring any inspiratory effort in which, between the start time and the end time of the inspiratory effort, a variation of the neural inspiration signal is less than a minimum signal variation threshold, wherein the trigger error is determined based on analysis of the neural inspiration signal and of the measurement signal between an end of a previous inspiratory effort of the patient and an end of the current inspiratory effort of the patient, wherein the start time of the ventilatory assist preceding the start time of the current inspiratory effort of the patient denotes an early trigger error and wherein the start time of the ventilatory assist following the start time of the current inspiratory effort of the patient denotes a late trigger error;

determining, based on the neural inspiration signal, a cycling-off error by comparing an end time of the current inspiratory effort of the patient with the end time of the ventilatory assist, wherein determining the cycling-off error comprises ignoring any inspiratory effort in which, between the start time and end time of the ventilatory assist, a variation of a pressure delivered by the ventilatory assist is less than a minimum pressure variation threshold, wherein the cycling-off error is determined based on analysis of the neural inspiration signal and of the measurement signal between a start of the current inspiratory effort of the patient and a start of a next inspiratory effort of the patient, wherein the end time of the ventilatory assist preceding the end time of the current inspiratory effort of the patient denotes an early cycling-off error and wherein the end time of the ventilatory assist following the end time of the current inspiratory effort of the patient denotes a late cycling-off error; and adjusting the ventilatory assist provided to the patient by the mechanical ventilator so that the trigger error is lower than a first threshold and the cycling-off error is lower than a second threshold.

2. The method of claim 1, wherein:
determining the trigger error further comprises normalizing the trigger error during an inspiratory test period; and
determining the cycling-off error further comprises normalizing the cycling-off error during an expiratory test period.

3. The method of claim 1, comprising:
determining the trigger error and the cycling-off error for a plurality of breaths;
for each of the plurality of breaths, determining that the ventilatory assist is synchronized when the trigger error is lower than the first threshold and the cycling-off error is lower than the second threshold; and
calculating a ratio of occurrences of breaths when the ventilatory assist is synchronized over occurrences of breaths when the ventilatory assist is not synchronized.

4. The method of claim 3, comprising characterizing the ventilatory assist according to an element selected from the group consisting of synchronized assist, late trigger with early cycling-off, late trigger with late cycling-off, early trigger with early cycling-off, early trigger with late cycling-off and unassisted inspiratory effort.

5. The method of claim 1, wherein the neural inspiration is measured from a diaphragm electrical activity (EAdi).

6. The method of claim 1, further comprising:
providing a range of trigger errors versus cycling-off errors on a graph;
defining on the graph a given area representing an acceptable limit of ventilatory assist synchronization wherein, in the given area, magnitudes of the trigger errors are lower than the first threshold and magnitudes of the cycling-off errors are lower than the second threshold;
for each particular breath of a plurality of breaths, placing on the graph a corresponding point representing the trigger error and the cycling-off error for the particular breath; and
for each particular breath, determining that the ventilatory assist is synchronized for the particular breath when the corresponding point is situated in a within the given area of the graph.

7. The method of claim 6, further comprising:
counting a first number of early trigger errors, a second number of late trigger errors, a third number of early cycling-off errors, and a fourth number of late cycling-off errors, the early trigger errors, the late trigger errors, the early cycling-off errors, and the late cycling-off errors falling outside said given area of the graph,
determining a most frequent error type based on a highest of the first, second, third, and fourth numbers, and
conducting instructions or actions to correct at least the errors of the most frequent error type.

8. The method of claim 7, further comprising, if said errors of the most frequent error type persist, repeating said instructions or actions to correct said errors of the most frequent error type.

9. The method of claim 7, further comprising, if said errors of the most frequent error type persist, introducing other instructions or actions in a stepwise fashion to correct said errors of the most frequent error type.

10. The method of claim 1, wherein the first threshold is not equal to the second threshold.

11. The method of claim 1, further comprising:
detecting a central apnea event of the patient based on a combination of an early trigger error and a late cycling-off error.

12. The method of claim 1, further comprising:
detecting a double-triggering event of the patient by detecting a sequence including (i) an early-trigger error, (ii) an early cycling-off error, (iii) a late trigger error, and (iv) a late cycling-off error.

13. The method of claim 1, further comprising:
detecting an auto-triggering event of the patient by detecting a sequence including at least (i) a first start, (ii) a first end, (iii) a second start, and (iv) a second end of the ventilatory assist, the sequence occurring without any inspiratory effort of the patient.

14. The method of claim 1, further comprising:
detecting a plurality of successive breaths delivered to the patient by the ventilatory support system concurrent with a single inspiratory effort of the patient.

15. A ventilatory support system, comprising:
one or more electrodes;
a mechanical ventilator configured to provide ventilatory assist to a patient;
a first interface for receiving, from the one or more electrodes, a neural inspiration signal representing an inspiratory effort of the patient;
a second interface for receiving, from the mechanical ventilator, a measurement signal representing a start time and an end time of the ventilatory assist;
a memory for storing a first threshold and a second threshold; and
a processor operatively coupled to the first and second interfaces and to the memory, the processor being configured to:
determine, based on the neural inspiration signal, a trigger error by comparing a start time of a current inspiratory effort of the patient with the start time of the ventilatory assist, wherein the processor is configured to determine the trigger error by ignoring any inspiratory effort in which, between the start time and the end time of the inspiratory effort, a variation of the neural inspiration signal is less than a minimum signal variation threshold, wherein the trigger error is determined based on analysis of the neural inspiration signal and of the measurement signal between an end of a previous inspiratory effort of the patient and an end of the current inspiratory effort of the patient, wherein the start time of the ventilatory assist preceding the start time of the current inspiratory effort of the patient denotes an early trigger error and wherein the start time of the ventilatory assist following the start time of the current inspiratory effort of the patient denotes a late trigger error,
determine, based on the neural inspiration signal, a cycling-off error by comparing an end time of the current inspiratory effort of the patient with the end time of the ventilatory assist, wherein the processor is configured to determine the cycling-off error by ignoring any inspiratory effort in which, between the start time and end time of the ventilatory assist, a variation of a pressure delivered by the ventilatory assist is less than a minimum pressure variation threshold, wherein the cycling-off error is determined based on analysis of the neural inspiration signal and of the measurement signal between a start of the current inspiratory effort of the patient and a start of a next inspiratory effort of the patient, wherein the end time of the ventilatory assist preceding the end time of the current inspiratory effort of the patient denotes an early cycling-off error and wherein the end time of the ventilatory assist following the end time of the current inspiratory effort of the patient denotes a late cycling-off error, and adjust the ventilatory assist provided to the patient by the mechanical ventilator so that the trigger error is lower than the first threshold and the cycling-off error is lower than the second threshold.

16. The system of claim 15, wherein the processor determines that ventilatory assist is synchronized when the trigger error and the cycling-off error correspond to a point situated in a given area of a graph of the trigger error versus the cycling-off error.

17. The system of claim 16, wherein:

the processor counts a first number of early trigger errors, a second number of late trigger errors, a third number of early cycling-off errors, and a fourth number of late cycling-off errors, the early trigger errors, the late trigger errors, the early cycling-off errors, and the late cycling-off errors falling outside said given area of the graph, the processor determines a most frequent error type based on a highest of the first, second, third, and fourth numbers, and the processor conducts instructions or actions to correct at least the errors of the most frequent error type.

18. The system of claim 17, wherein the processor is configured to repeat said instructions or actions to correct said errors of the most frequent error type when said errors of the most frequent error type persist.

19. The system of claim 17, wherein the processor is configured to introduce other instructions or actions in a stepwise fashion to correct said errors of the most frequent error type when said errors of the most frequent error type persist.

20. The system of claim 15, wherein the processor is configured to:

normalize the trigger error during an inspiratory test period; and normalize the cycling-off error during an expiratory test period.

21. The system of claim 15, wherein the neural inspiration signal represents an electrical activity (EAdi) of the patient's diaphragm.

22. The system of claim 15, comprising a display for displaying a graphical presentation of the trigger and of the cycling-off error.

23. The system of claim 15, wherein the first threshold is not equal to the second threshold.

* * * * *